United States Patent [19]
Penaud

[11] Patent Number: 6,025,187
[45] Date of Patent: Feb. 15, 2000

[54] COMBINATIONS OF BACILLUS AND LACTOBACILLUS SPECIES FOR PRODUCING PROTEIN FROM WASTE

[75] Inventor: Jean Penaud, Tours, France

[73] Assignee: Cobiotex, Rennes-Chantepie, France

[21] Appl. No.: 08/584,382

[22] Filed: Jan. 11, 1996

[30] Foreign Application Priority Data

Jan. 9, 1995 [FR] France ................... 95 00162

[51] Int. Cl.$^7$ .................. B09B 3/00; C12N 1/20
[52] U.S. Cl. ............ 435/262.5; 210/611; 435/252.4; 435/252.5; 435/252.9; 435/822
[58] Field of Search .................. 435/252.4, 822, 435/252.5, 252.9, 262.5; 424/93.3, 93.45, 93.46, 718; 426/41; 210/611

[56] References Cited

U.S. PATENT DOCUMENTS

| | | | |
|---|---|---|---|
| 3,961,078 | 6/1976 | Stitt ........................... | 426/41 |
| 4,148,689 | 4/1979 | Hino et al. ................. | 195/65 |
| 4,314,904 | 2/1982 | Fedde et al. ............... | 210/611 |
| 5,445,952 | 8/1995 | Campbell et al. ......... | 435/121 |

OTHER PUBLICATIONS

JAPIO, AN 84–013175, JP–A–59 013 175, Jan. 23, 1984.
JAPIO, AN 93–078663, JP–A–05 078 663, Mar. 30, 1993.
JAPIO, AN 85–012198, JP–A–60 012 198, Jan. 22, 1985.
JAPIO, AN 89–211487, JP–A–01 211 487, Aug. 24, 1989.

*Primary Examiner*—David M. Naff
*Assistant Examiner*—Deborah K. Ware
*Attorney, Agent, or Firm*—Oblon, Spivak, McClelland, Maier & Neustadt, P.C.

[57] ABSTRACT

Bacterial complexes are provided which may be used in the digestion and decomposition of residues of biological origin in the form of biomass, and the transformation of these residues into non-polluting organic compounds. Also provided are the applications of these bacterial complexes to the treatment of waste of biological origin such as excrement (pig, ruminant, equid, or poultry litter), liquid manures, corpses, and stagnant waters. In these applications, this waste is converted into compost or other stable, biodegradable, and non-polluting nitrogenous compounds. The bacterial complexes essentially contain at least one non-pathogenic Bacillus and at least one non-pathogenic Lactobacillus. These bacterial complexes are capable of converting inorganic nitrogen, in particular aqueous ammonia, nitrates, nitrites, and organic nitrogen molecules (such as urea, urates, amino acids, nitrogenous bases, or any other nitrogenous compounds of low molecular weight) into organic nitrogen in the form of bacterial proteins. The bacterial complexes may also contain comprise Pediococcus.

26 Claims, 29 Drawing Sheets

STRAIN CODE: ISB 02

|   |                     | CODE |               | CODE |
|---|---------------------|------|---------------|------|
|   | GLYCEROL            | +    | SALICIN       | +    |
| 5 | ERYTHRITOL          | −    | CELLOBIOSE    | +    |
|   | D-ARABINOSE         | −    | MALTOSE       | +    |
|   | L-ARABINOSE         | +    | LACTOSE       | +    |
|   | RIBOSE              | +    | MELIBIOSE     | +    |
|   | D-XYLOSE            | +    | SACCHAROSE    | +    |
|10 | L-XYLOSE            | −    | TREHALOSE     | +    |
|   | ADONITOL            | −    | INULIN        | +    |
|   | β-METHYLXYLOSIDE    | −    | MELEZITOSE    | −    |
|   | GALACTOSE           | ±    | D-RAFFINOSE   | +    |
|   | D-GLUCOSE           | +    | STARCH        | +    |
|15 | D-FRUCTOSE          | +    | GLYCOGEN      | +    |
|   | D-MANNOSE           | +    | XYLITOL       | −    |
|   | L-SORBOSE           | −    | β-GENTIOBIOSE | +    |
|   | RHAMNOSE            | ±    | D-TURANOSE    | +    |
|   | DULCITOL            | −    | D-LYXOSE      | −    |
|20 | INOSITOL            | +    | D-TAGATOSE    | −    |
|   | MANNITOL            | +    | D-FUCOSE      | −    |
|   | SORBITOL            | +    | L-FUCOSE      | −    |
|   | α-METHYL-D-MANNOSIDE| −    | D-ARABITOL    | −    |
|   | α-METHYL-D-GLUCOSIDE| +    | L-ARABITOL    | −    |
|25 | N-ACETYLGLUCOSAMINE | −    | GLUCONATE     | −    |
|   | AMYGDALIN           | +    | 2-KETOGLUCONATE | −  |
|   | ARBUTIN             | +    | 5-KETOGLUCONATE | −  |
|   | ESCULIN             | +    |               |      |

*FIG. 1*

STRAIN CODE: ISB 09

|   |                    | CODE |                | CODE |
|---|--------------------|------|----------------|------|
|   | GLYCEROL           | +    | SALICIN        | +    |
| 5 | ERYTHRITOL         | −    | CELLOBIOSE     | +    |
|   | D-ARABINOSE        | −    | MALTOSE        | +    |
|   | L-ARABINOSE        | +    | LACTOSE        | −    |
|   | RIBOSE             | +    | MELIBIOSE      | +    |
|   | D-XYLOSE           | −    | SACCHAROSE     | +    |
| 10| L-XYLOSE           | −    | TREHALOSE      | +    |
|   | ADONITOL           | −    | INULIN         | +    |
|   | β-METHYLXYLOSIDE   | −    | MELEZITOSE     | −    |
|   | GALACTOSE          | −    | D-RAFFINOSE    | +    |
|   | D-GLUCOSE          | +    | STARCH         | +    |
| 15| D-FRUCTOSE         | +    | GLYCOGEN       | +    |
|   | D-MANNOSE          | +    | XYLITOL        | −    |
|   | L-SORBOSE          | −    | β-GENTIOBIOSE  | +    |
|   | RHAMNOSE           | −    | D-TURANOSE     | −    |
|   | DULCITOL           | −    | D-LYXOSE       | −    |
| 20| INOSITOL           | +    | D-TAGATOSE     | −    |
|   | MANNITOL           | +    | D-FUCOSE       | −    |
|   | SORBITOL           | +    | L-FUCOSE       | −    |
|   | α-METHYL-D-MANNOSIDE| −   | D-ARABITOL     | −    |
|   | α-METHYL-D-GLUCOSIDE| +   | L-ARABITOL     | −    |
| 25| N-ACETYLGLUCOSAMINE| −    | GLUCONATE      | −    |
|   | AMYGDALIN          | +    | 2-KETOGLUCONATE| −    |
|   | ARBUTIN            | +    | 5-KETOGLUCONATE| −    |
|   | ESCULIN            | +    |                |      |
|   |                    |      |                |      |
| 30|                    |      |                |      |

FIG. 2

STRAIN CODE: ISB 12

|  | CODE |  | CODE |
|---|---|---|---|
| GLYCEROL | + | SALICIN | + |
| ERYTHRITOL | − | CELLOBIOSE | + |
| D-ARABINOSE | − | MALTOSE | + |
| L-ARABINOSE | + | LACTOSE | + |
| RIBOSE | + | MELIBIOSE | − |
| D-XYLOSE | + | SACCHAROSE | + |
| L-XYLOSE | − | TREHALOSE | + |
| ADONITOL | − | INULIN | − |
| β-METHYLXYLOSIDE | − | MELEZITOSE | − |
| GALACTOSE | − | D-RAFFINOSE | + |
| D-GLUCOSE | + | STARCH | + |
| D-FRUCTOSE | + | GLYCOGEN | + |
| D-MANNOSE | + | XYLITOL | − |
| L-SORBOSE | − | β-GENTIOBIOSE | + |
| RHAMNOSE | − | D-TURANOSE | + |
| DULCITOL | − | D-LYXOSE | − |
| INOSITOL | + | D-TAGATOSE | − |
| MANNITOL | + | D-FUCOSE | − |
| SORBITOL | + | L-FUCOSE | − |
| α-METHYL-D-MANNOSIDE | − | D-ARABITOL | − |
| α-METHYL-D-GLUCOSIDE | + | L-ARABITOL | − |
| N-ACETYLGLUCOSAMINE | − | GLUCONATE | − |
| AMYGDALIN | + | 2-KETOGLUCONATE | − |
| ARBUTIN | + | 5-KETOGLUCONATE | − |
| ESCULIN | + |  |  |

*FIG. 3*

STRAIN CODE: ISB 04

|  | | CODE | | CODE |
|---|---|---|---|---|
|  | GLYCEROL | + | SALICIN | + |
|  | ERYTHRITOL | – | CELLOBIOSE | + |
|  | D-ARABINOSE | – | MALTOSE | + |
|  | L-ARABINOSE | + | LACTOSE | + |
|  | RIBOSE | + | MELIBIOSE | + |
|  | D-XYLOSE | + | SACCHAROSE | + |
|  | L-XYLOSE | – | TREHALOSE | + |
|  | ADONITOL | – | INULIN | – |
|  | β-METHYLXYLOSIDE | – | MELEZITOSE | – |
|  | GALACTOSE | – | D-RAFFINOSE | + |
|  | D-GLUCOSE | + | STARCH | + |
|  | D-FRUCTOSE | + | GLYCOGEN | + |
|  | D-MANNOSE | + | XYLITOL | – |
|  | L-SORBOSE | – | β-GENTIOBIOSE | + |
|  | RHAMNOSE | – | D-TURANOSE | + |
|  | DULCITOL | – | D-LYXOSE | – |
|  | INOSITOL | + | D-TAGATOSE | – |
|  | MANNITOL | + | D-FUCOSE | – |
|  | SORBITOL | + | L-FUCOSE | – |
|  | α-METHYL-D-MANNOSIDE | – | D-ARABITOL | – |
|  | α-METHYL-D-GLUCOSIDE | + | L-ARABITOL | – |
|  | N-ACETYLGLUCOSAMINE | – | GLUCONATE | – |
|  | AMYGDALIN | + | 2-KETOGLUCONATE | – |
|  | ARBUTIN | + | 5-KETOGLUCONATE | – |
|  | ESCULIN | + |  |  |

*FIG. 4*

STRAIN CODE: ISB 05

|  | | CODE | | CODE |
|---|---|---|---|---|
| 5 | GLYCEROL | + | SALICIN | + |
|  | ERYTHRITOL | − | CELLOBIOSE | + |
|  | D-ARABINOSE | − | MALTOSE | + |
|  | L-ARABINOSE | + | LACTOSE | + |
|  | RIBOSE | + | MELIBIOSE | + |
|  | D-XYLOSE | + | SACCHAROSE | + |
| 10 | L-XYLOSE | − | TREHALOSE | + |
|  | ADONITOL | − | INULIN | − |
|  | β-METHYLXYLOSIDE | + | MELEZITOSE | − |
|  | GALACTOSE | − | D-RAFFINOSE | + |
|  | D-GLUCOSE | + | STARCH | + |
| 15 | D-FRUCTOSE | + | GLYCOGEN | + |
|  | D-MANNOSE | + | XYLITOL | + |
|  | L-SORBOSE | − | β-GENTIOBIOSE | + |
|  | RHAMNOSE | − | D-TURANOSE | − |
|  | DULCITOL | − | D-LYXOSE | − |
| 20 | INOSITOL | + | D-TAGATOSE | − |
|  | MANNITOL | + | D-FUCOSE | − |
|  | SORBITOL | + | L-FUCOSE | − |
|  | α-METHYL-D-MANNOSIDE | − | D-ARABITOL | − |
|  | α-METHYL-D-GLUCOSIDE | + | L-ARABITOL | − |
| 25 | N-ACETYLGLUCOSAMINE | + | GLUCONATE | − |
|  | AMYGDALIN | + | 2-KETOGLUCONATE | − |
|  | ARBUTIN | + | 5-KETOGLUCONATE | − |
|  | ESCULIN | + | | |

*FIG. 5*

STRAIN CODE: ISB 06

| | | CODE | | CODE |
|---|---|---|---|---|
| | GLYCEROL | + | SALICIN | + |
| 5 | ERYTHRITOL | − | CELLOBIOSE | + |
| | D-ARABINOSE | − | MALTOSE | + |
| | L-ARABINOSE | + | LACTOSE | + |
| | RIBOSE | − | MELIBIOSE | + |
| | D-XYLOSE | − | SACCHAROSE | + |
| 10 | L-XYLOSE | − | TREHALOSE | + |
| | ADONITOL | − | INULIN | − |
| | β-METHYLXYLOSIDE | − | MELEZITOSE | − |
| | GALACTOSE | − | D-RAFFINOSE | − |
| | D-GLUCOSE | + | STARCH | + |
| 15 | D-FRUCTOSE | + | GLYCOGEN | + |
| | D-MANNOSE | + | XYLITOL | − |
| | L-SORBOSE | − | β-GENTIOBIOSE | + |
| | RHAMNOSE | − | D-TURANOSE | − |
| | DULCITOL | − | D-LYXOSE | − |
| 20 | INOSITOL | + | D-TAGATOSE | − |
| | MANNITOL | + | D-FUCOSE | − |
| | SORBITOL | + | L-FUCOSE | − |
| | α-METHYL-D-MANNOSIDE | − | D-ARABITOL | − |
| | α-METHYL-D-GLUCOSIDE | + | L-ARABITOL | − |
| 25 | N-ACETYLGLUCOSAMINE | − | GLUCONATE | − |
| | AMYGDALIN | + | 2-KETOGLUCONATE | − |
| | ARBUTIN | + | 5-KETOGLUCONATE | − |
| | ESCULIN | + | | |

*FIG. 6*

STRAIN CODE: ISB 07

| | | CODE | | CODE |
|---|---|---|---|---|
| | GLYCEROL | + | SALICIN | + |
| 5 | ERYTHRITOL | - | CELLOBIOSE | + |
| | D-ARABINOSE | - | MALTOSE | + |
| | L-ARABINOSE | + | LACTOSE | + |
| | RIBOSE | + | MELIBIOSE | - |
| | D-XYLOSE | + | SACCHAROSE | + |
| 10 | L-XYLOSE | - | TREHALOSE | + |
| | ADONITOL | - | INULIN | - |
| | β-METHYLXYLOSIDE | - | MELEZITOSE | - |
| | GALACTOSE | - | D-RAFFINOSE | + |
| | D-GLUCOSE | + | STARCH | + |
| 15 | D-FRUCTOSE | + | GLYCOGEN | + |
| | D-MANNOSE | + | XYLITOL | - |
| | L-SORBOSE | - | β-GENTIOBIOSE | + |
| | RHAMNOSE | - | D-TURANOSE | - |
| | DULCITOL | - | D-LYXOSE | - |
| 20 | INOSITOL | + | D-TAGATOSE | - |
| | MANNITOL | + | D-FUCOSE | - |
| | SORBITOL | + | L-FUCOSE | - |
| | α-METHYL-D-MANNOSIDE | - | D-ARABITOL | - |
| | α-METHYL-D-GLUCOSIDE | + | L-ARABITOL | - |
| 25 | N-ACETYLGLUCOSAMINE | - | GLUCONATE | - |
| | AMYGDALIN | + | 2-KETOGLUCONATE | - |
| | ARBUTIN | + | 5-KETOGLUCONATE | - |
| | ESCULIN | + | | |

*FIG. 7*

STRAIN CODE: ISB 11

| | CODE | | CODE |
|---|---|---|---|
| GLYCEROL | + | SALICIN | + |
| ERYTHRITOL | - | CELLOBIOSE | + |
| D-ARABINOSE | - | MALTOSE | + |
| L-ARABINOSE | + | LACTOSE | + |
| RIBOSE | + | MELIBIOSE | + |
| D-XYLOSE | + | SACCHAROSE | + |
| L-XYLOSE | - | TREHALOSE | + |
| ADONITOL | - | INULIN | + |
| β-METHYLXYLOSIDE | + | MELEZITOSE | + |
| GALACTOSE | + | D-RAFFINOSE | + |
| D-GLUCOSE | + | STARCH | + |
| D-FRUCTOSE | + | GLYCOGEN | + |
| D-MANNOSE | + | XYLITOL | - |
| L-SORBOSE | - | β-GENTIOBIOSE | + |
| RHAMNOSE | - | D-TURANOSE | + |
| DULCITOL | - | D-LYXOSE | - |
| INOSITOL | - | D-TAGATOSE | - |
| MANNITOL | + | D-FUCOSE | - |
| SORBITOL | - | L-FUCOSE | - |
| α-METHYL-D-MANNOSIDE | - | D-ARABITOL | - |
| α-METHYL-D-GLUCOSIDE | + | L-ARABITOL | - |
| N-ACETYLGLUCOSAMINE | + | GLUCONATE | - |
| AMYGDALIN | + | 2-KETOGLUCONATE | - |
| ARBUTIN | + | 5-KETOGLUCONATE | - |
| ESCULIN | + | | |

*FIG. 8*

STRAIN CODE: ISL 01

|   |                      | CODE |                | CODE |
|---|----------------------|------|----------------|------|
|   | GLYCEROL             | −    | SALICIN        | +    |
| 5 | ERYTHRITOL           | −    | CELLOBIOSE     | +    |
|   | D-ARABINOSE          | −    | MALTOSE        | +    |
|   | L-ARABINOSE          | −    | LACTOSE        | +    |
|   | RIBOSE               | +    | MELIBIOSE      | −    |
|   | D-XYLOSE             | −    | SACCHAROSE     | +    |
| 10| L-XYLOSE             | −    | TREHALOSE      | +    |
|   | ADONITOL             | −    | INULIN         | −    |
|   | β-METHYLXYLOSIDE     | −    | MELEZITOSE     | +    |
|   | GALACTOSE            | +    | D-RAFFINOSE    | −    |
|   | D-GLUCOSE            | +    | STARCH         | −    |
| 15| D-FRUCTOSE           | +    | GLYCOGEN       | −    |
|   | D-MANNOSE            | +    | XYLITOL        | −    |
|   | L-SORBOSE            | −    | β-GENTIOBIOSE  | +    |
|   | RHAMNOSE             | +    | D-TURANOSE     | ±    |
|   | DULCITOL             | −    | D-LYXOSE       | −    |
| 20| INOSITOL             | −    | D-TAGATOSE     | +    |
|   | MANNITOL             | +    | D-FUCOSE       | −    |
|   | SORBITOL             | +    | L-FUCOSE       | −    |
|   | α-METHYL-D-MANNOSIDE | −    | D-ARABITOL     | −    |
|   | α-METHYL-D-GLUCOSIDE | +    | L-ARABITOL     | −    |
| 25| N-ACETYLGLUCOSAMINE  | +    | GLUCONATE      | +    |
|   | AMYGDALIN            | +    | 2-KETOGLUCONATE| −    |
|   | ARBUTIN              | +    | 5-KETOGLUCONATE| −    |
|   | ESCULIN              | +    |                |      |

*FIG. 9*

STRAIN CODE: ISL 05

| | CODE | | CODE |
|---|---|---|---|
| GLYCEROL | − | SALICIN | + |
| ERYTHRITOL | − | CELLOBIOSE | + |
| D-ARABINOSE | − | MALTOSE | + |
| L-ARABINOSE | − | LACTOSE | + |
| RIBOSE | + | MELIBIOSE | − |
| D-XYLOSE | − | SACCHAROSE | ± |
| L-XYLOSE | − | TREHALOSE | + |
| ADONITOL | − | INULIN | − |
| β-METHYLXYLOSIDE | − | MELEZITOSE | + |
| GALACTOSE | + | D-RAFFINOSE | − |
| D-GLUCOSE | + | STARCH | − |
| D-FRUCTOSE | + | GLYCOGEN | − |
| D-MANNOSE | + | XYLITOL | − |
| L-SORBOSE | + | β-GENTIOBIOSE | + |
| RHAMNOSE | + | D-TURANOSE | + |
| DULCITOL | − | D-LYXOSE | − |
| INOSITOL | ± | D-TAGATOSE | + |
| MANNITOL | + | D-FUCOSE | − |
| SORBITOL | + | L-FUCOSE | − |
| α-METHYL-D-MANNOSIDE | − | D-ARABITOL | − |
| α-METHYL-D-GLUCOSIDE | + | L-ARABITOL | − |
| N-ACETYLGLUCOSAMINE | + | GLUCONATE | + |
| AMYGDALIN | + | 2-KETOGLUCONATE | − |
| ARBUTIN | + | 5-KETOGLUCONATE | − |
| ESCULIN | + | | |

*FIG. 10*

STRAIN CODE: ISL 10

|    |                    | CODE |               | CODE |
|----|--------------------|------|---------------|------|
|    | GLYCEROL           | −    | SALICIN       | +    |
| 5  | ERYTHRITOL         | −    | CELLOBIOSE    | +    |
|    | D-ARABINOSE        | −    | MALTOSE       | +    |
|    | L-ARABINOSE        | −    | LACTOSE       | +    |
|    | RIBOSE             | +    | MELIBIOSE     | −    |
|    | D-XYLOSE           | −    | SACCHAROSE    | +    |
| 10 | L-XYLOSE           | −    | TREHALOSE     | +    |
|    | ADONITOL           | −    | INULIN        | −    |
|    | β-METHYLXYLOSIDE   | −    | MELEZITOSE    | +    |
|    | GALACTOSE          | +    | D-RAFFINOSE   | −    |
|    | D-GLUCOSE          | +    | STARCH        | −    |
| 15 | D-FRUCTOSE         | +    | GLYCOGEN      | −    |
|    | D-MANNOSE          | +    | XYLITOL       | −    |
|    | L-SORBOSE          | −    | β-GENTIOBIOSE | +    |
|    | RHAMNOSE           | +    | D-TURANOSE    | +    |
|    | DULCITOL           | −    | D-LYXOSE      | −    |
| 20 | INOSITOL           | −    | D-TAGATOSE    | +    |
|    | MANNITOL           | +    | D-FUCOSE      | −    |
|    | SORBITOL           | +    | L-FUCOSE      | −    |
|    | α-METHYL-D-MANNOSIDE | −  | D-ARABITOL    | −    |
|    | α-METHYL-D-GLUCOSIDE | +  | L-ARABITOL    | −    |
| 25 | N-ACETYLGLUCOSAMINE | +   | GLUCONATE     | +    |
|    | AMYGDALIN          | +    | 2-KETOGLUCONATE | −  |
|    | ARBUTIN            | +    | 5-KETOGLUCONATE | −  |
|    | ESCULIN            | +    |               |      |

*FIG. 11*

STRAIN CODE: ISL 20

|  | CODE |  | CODE |
|---|---|---|---|
| GLYCEROL | − | SALICIN | + |
| ERYTHRITOL | − | CELLOBIOSE | + |
| D-ARABINOSE | − | MALTOSE | + |
| L-ARABINOSE | − | LACTOSE | + |
| RIBOSE | + | MELIBIOSE | − |
| D-XYLOSE | − | SACCHAROSE | ± |
| L-XYLOSE | − | TREHALOSE | + |
| ADONITOL | − | INULIN | − |
| β-METHYLXYLOSIDE | − | MELEZITOSE | + |
| GALACTOSE | + | D-RAFFINOSE | − |
| D-GLUCOSE | + | STARCH | − |
| D-FRUCTOSE | + | GLYCOGEN | − |
| D-MANNOSE | + | XYLITOL | − |
| L-SORBOSE | + | β-GENTIOBIOSE | ± |
| RHAMNOSE | + | D-TURANOSE | ± |
| DULCITOL | − | D-LYXOSE | − |
| INOSITOL | − | D-TAGATOSE | + |
| MANNITOL | + | D-FUCOSE | − |
| SORBITOL | + | L-FUCOSE | − |
| α-METHYL-D-MANNOSIDE | − | D-ARABITOL | − |
| α-METHYL-D-GLUCOSIDE | + | L-ARABITOL | − |
| N-ACETYLGLUCOSAMINE | + | GLUCONATE | + |
| AMYGDALIN | + | 2-KETOGLUCONATE | − |
| ARBUTIN | + | 5-KETOGLUCONATE | − |
| ESCULIN | + |  |  |

*FIG. 12*

STRAIN CODE: ISL 21

| | CODE | | CODE |
|---|---|---|---|
| GLYCEROL | − | SALICIN | + |
| ERYTHRITOL | − | CELLOBIOSE | + |
| D-ARABINOSE | − | MALTOSE | + |
| L-ARABINOSE | − | LACTOSE | + |
| RIBOSE | + | MELIBIOSE | − |
| D-XYLOSE | − | SACCHAROSE | + |
| L-XYLOSE | − | TREHALOSE | + |
| ADONITOL | − | INULIN | − |
| β-METHYLXYLOSIDE | − | MELEZITOSE | + |
| GALACTOSE | + | D-RAFFINOSE | − |
| D-GLUCOSE | + | STARCH | − |
| D-FRUCTOSE | + | GLYCOGEN | − |
| D-MANNOSE | + | XYLITOL | − |
| L-SORBOSE | + | β-GENTIOBIOSE | + |
| RHAMNOSE | + | D-TURANOSE | + |
| DULCITOL | − | D-LYXOSE | − |
| INOSITOL | − | D-TAGATOSE | + |
| MANNITOL | + | D-FUCOSE | − |
| SORBITOL | − | L-FUCOSE | − |
| α-METHYL-D-MANNOSIDE | − | D-ARABITOL | − |
| α-METHYL-D-GLUCOSIDE | + | L-ARABITOL | − |
| N-ACETYLGLUCOSAMINE | + | GLUCONATE | + |
| AMYGDALIN | + | 2-KETOGLUCONATE | − |
| ARBUTIN | + | 5-KETOGLUCONATE | − |
| ESCULIN | + | | |

*FIG. 13*

STRAIN CODE: ISL 25

|  |  | CODE |  | CODE |
|---|---|---|---|---|
|  | GLYCEROL | − | SALICIN | + |
| 5 | ERYTHRITOL | − | CELLOBIOSE | + |
|  | D-ARABINOSE | − | MALTOSE | + |
|  | L-ARABINOSE | − | LACTOSE | + |
|  | RIBOSE | + | MELIBIOSE | − |
|  | D-XYLOSE | − | SACCHAROSE | + |
| 10 | L-XYLOSE | − | TREHALOSE | + |
|  | ADONITOL | − | INULIN | − |
|  | β-METHYLXYLOSIDE | − | MELEZITOSE | + |
|  | GALACTOSE | + | D-RAFFINOSE | − |
|  | D-GLUCOSE | + | STARCH | − |
| 15 | D-FRUCTOSE | + | GLYCOGEN | − |
|  | D-MANNOSE | + | XYLITOL | − |
|  | L-SORBOSE | + | β-GENTIOBIOSE | ± |
|  | RHAMNOSE | + | D-TURANOSE | + |
|  | DULCITOL | − | D-LYXOSE | − |
| 20 | INOSITOL | ± | D-TAGATOSE | + |
|  | MANNITOL | + | D-FUCOSE | − |
|  | SORBITOL | + | L-FUCOSE | − |
|  | α-METHYL-D-MANNOSIDE | − | D-ARABITOL | − |
|  | α-METHYL-D-GLUCOSIDE | + | L-ARABITOL | − |
| 25 | N-ACETYLGLUCOSAMINE | + | GLUCONATE | + |
|  | AMYGDALIN | − | 2-KETOGLUCONATE | − |
|  | ARBUTIN | + | 5-KETOGLUCONATE | − |
|  | ESCULIN | + |  |  |

*FIG. 14*

STRAIN CODE: ISL 35

|  | | CODE | | CODE |
|---|---|---|---|---|
|  | GLYCEROL | − | SALICIN | + |
| 5 | ERYTHRITOL | − | CELLOBIOSE | + |
|  | D-ARABINOSE | − | MALTOSE | + |
|  | L-ARABINOSE | − | LACTOSE | + |
|  | RIBOSE | + | MELIBIOSE | − |
|  | D-XYLOSE | − | SACCHAROSE | + |
| 10 | L-XYLOSE | − | TREHALOSE | + |
|  | ADONITOL | − | INULIN | − |
|  | β-METHYLXYLOSIDE | − | MELEZITOSE | + |
|  | GALACTOSE | + | D-RAFFINOSE | ± |
|  | D-GLUCOSE | + | STARCH | − |
| 15 | D-FRUCTOSE | + | GLYCOGEN | − |
|  | D-MANNOSE | + | XYLITOL | − |
|  | L-SORBOSE | − | β-GENTIOBIOSE | − |
|  | RHAMNOSE | + | D-TURANOSE | − |
|  | DULCITOL | − | D-LYXOSE | − |
| 20 | INOSITOL | − | D-TAGATOSE | + |
|  | MANNITOL | + | D-FUCOSE | − |
|  | SORBITOL | + | L-FUCOSE | − |
|  | α-METHYL-D-MANNOSIDE | − | D-ARABITOL | − |
|  | α-METHYL-D-GLUCOSIDE | + | L-ARABITOL | − |
| 25 | N-ACETYLGLUCOSAMINE | + | GLUCONATE | + |
|  | AMYGDALIN | + | 2-KETOGLUCONATE | − |
|  | ARBUTIN | + | 5-KETOGLUCONATE | − |
|  | ESCULIN | + |  |  |

*FIG. 15*

STRAIN CODE: ISL 03

|  | CODE |  | CODE |
|---|---|---|---|
| GLYCEROL | − | SALICIN | + |
| ERYTHRITOL | − | CELLOBIOSE | + |
| D-ARABINOSE | − | MALTOSE | − |
| L-ARABINOSE | − | LACTOSE | + |
| RIBOSE | − | MELIBIOSE | − |
| D-XYLOSE | − | SACCHAROSE | − |
| L-XYLOSE | − | TREHALOSE | + |
| ADONITOL | + | INULIN | − |
| β-METHYLXYLOSIDE | − | MELEZITOSE | + |
| GALACTOSE | + | D-RAFFINOSE | − |
| D-GLUCOSE | + | STARCH | − |
| D-FRUCTOSE | + | GLYCOGEN | − |
| D-MANNOSE | + | XYLITOL | − |
| L-SORBOSE | − | β-GENTIOBIOSE | + |
| RHAMNOSE | − | D-TURANOSE | − |
| DULCITOL | − | D-LYXOSE | − |
| INOSITOL | − | D-TAGATOSE | + |
| MANNITOL | ± | D-FUCOSE | − |
| SORBITOL | + | L-FUCOSE | − |
| α-METHYL-D-MANNOSIDE | − | D-ARABITOL | − |
| α-METHYL-D-GLUCOSIDE | − | L-ARABITOL | − |
| N-ACETYLGLUCOSAMINE | + | GLUCONATE | ± |
| AMYGDALIN | + | 2-KETOGLUCONATE | − |
| ARBUTIN | + | 5-KETOGLUCONATE | − |
| ESCULIN | + |  |  |

*FIG. 16*

STRAIN CODE: ISL 27

|  |  | CODE |  | CODE |
|---|---|---|---|---|
|  | GLYCEROL | − | SALICIN | + |
| 5 | ERYTHRITOL | − | CELLOBIOSE | + |
|  | D-ARABINOSE | − | MALTOSE | + |
|  | L-ARABINOSE | − | LACTOSE | + |
|  | RIBOSE | − | MELIBIOSE | − |
|  | D-XYLOSE | − | SACCHAROSE | − |
| 10 | L-XYLOSE | − | TREHALOSE | + |
|  | ADONITOL | + | INULIN | − |
|  | β-METHYLXYLOSIDE | − | MELEZITOSE | + |
|  | GALACTOSE | + | D-RAFFINOSE | − |
|  | D-GLUCOSE | + | STARCH | − |
| 15 | D-FRUCTOSE | + | GLYCOGEN | − |
|  | D-MANNOSE | + | XYLITOL | − |
|  | L-SORBOSE | − | β-GENTIOBIOSE | + |
|  | RHAMNOSE | − | D-TURANOSE | − |
|  | DULCITOL | − | D-LYXOSE | − |
| 20 | INOSITOL | ± | D-TAGATOSE | + |
|  | MANNITOL | + | D-FUCOSE | − |
|  | SORBITOL | + | L-FUCOSE | − |
|  | α-METHYL-D-MANNOSIDE | − | D-ARABITOL | − |
|  | α-METHYL-D-GLUCOSIDE | − | L-ARABITOL | − |
| 25 | N-ACETYLGLUCOSAMINE | + | GLUCONATE | + |
|  | AMYGDALIN | + | 2-KETOGLUCONATE | − |
|  | ARBUTIN | + | 5-KETOGLUCONATE | − |
|  | ESCULIN | + |  |  |

*FIG. 17*

STRAIN CODE: ISL 32

|  | CODE |  | CODE |
|---|---|---|---|
| GLYCEROL | − | SALICIN | + |
| ERYTHRITOL | − | CELLOBIOSE | + |
| D-ARABINOSE | − | MALTOSE | ± |
| L-ARABINOSE | − | LACTOSE | + |
| RIBOSE | − | MELIBIOSE | − |
| D-XYLOSE | − | SACCHAROSE | − |
| L-XYLOSE | − | TREHALOSE | + |
| ADONITOL | + | INULIN | − |
| β-METHYLXYLOSIDE | − | MELEZITOSE | + |
| GALACTOSE | + | D-RAFFINOSE | − |
| D-GLUCOSE | + | STARCH | − |
| D-FRUCTOSE | + | GLYCOGEN | − |
| D-MANNOSE | + | XYLITOL | − |
| L-SORBOSE | − | β-GENTIOBIOSE | + |
| RHAMNOSE | − | D-TURANOSE | − |
| DULCITOL | − | D-LYXOSE | − |
| INOSITOL | − | D-TAGATOSE | + |
| MANNITOL | + | D-FUCOSE | − |
| SORBITOL | + | L-FUCOSE | − |
| α-METHYL-D-MANNOSIDE | − | D-ARABITOL | − |
| α-METHYL-D-GLUCOSIDE | − | L-ARABITOL | − |
| N-ACETYLGLUCOSAMINE | + | GLUCONATE | + |
| AMYGDALIN | + | 2-KETOGLUCONATE | − |
| ARBUTIN | + | 5-KETOGLUCONATE | − |
| ESCULIN | + |  |  |

*FIG. 18*

STRAIN CODE: ISL 44

| | CODE | | CODE |
|---|---|---|---|
| GLYCEROL | - | SALICIN | + |
| ERYTHRITOL | - | CELLOBIOSE | + |
| D-ARABINOSE | - | MALTOSE | + |
| L-ARABINOSE | - | LACTOSE | + |
| RIBOSE | - | MELIBIOSE | - |
| D-XYLOSE | - | SACCHAROSE | + |
| L-XYLOSE | - | TREHALOSE | + |
| ADONITOL | | INULIN | - |
| β-METHYLXYLOSIDE | - | MELEZITOSE | - |
| GALACTOSE | + | D-RAFFINOSE | - |
| D-GLUCOSE | + | STARCH | - |
| D-FRUCTOSE | + | GLYCOGEN | - |
| D-MANNOSE | + | XYLITOL | - |
| L-SORBOSE | - | β-GENTIOBIOSE | + |
| RHAMNOSE | - | D-TURANOSE | + |
| DULCITOL | - | D-LYXOSE | - |
| INOSITOL | - | D-TAGATOSE | + |
| MANNITOL | - | D-FUCOSE | - |
| SORBITOL | - | L-FUCOSE | - |
| α-METHYL-D-MANNOSIDE | - | D-ARABITOL | - |
| α-METHYL-D-GLUCOSIDE | - | L-ARABITOL | - |
| N-ACETYLGLUCOSAMINE | + | GLUCONATE | - |
| AMYGDALIN | + | 2-KETOGLUCONATE | - |
| ARBUTIN | + | 5-KETOGLUCONATE | - |
| ESCULIN | + | | |

*FIG. 19*

STRAIN CODE: ISL 102

|  | CODE |  | CODE |
|---|---|---|---|
| GLYCEROL | − | SALICIN | − |
| ERYTHRITOL | − | CELLOBIOSE | − |
| D-ARABINOSE | − | MALTOSE | + |
| L-ARABINOSE | + | LACTOSE | − |
| RIBOSE | + | MELIBIOSE | − |
| D-XYLOSE | − | SACCHAROSE | + |
| L-XYLOSE | − | TREHALOSE | − |
| ADONITOL | − | INULIN | − |
| β-METHYLXYLOSIDE | − | MELEZITOSE | − |
| GALACTOSE | + | D-RAFFINOSE | + |
| D-GLUCOSE | + | STARCH | − |
| D-FRUCTOSE | + | GLYCOGEN | − |
| D-MANNOSE | − | XYLITOL | − |
| L-SORBOSE | − | β-GENTIOBIOSE | − |
| RHAMNOSE | − | D-TURANOSE | − |
| DULCITOL | − | D-LYXOSE | − |
| INOSITOL | − | D-TAGATOSE | − |
| MANNITOL | − | D-FUCOSE | − |
| SORBITOL | − | L-FUCOSE | − |
| α-METHYL-D-MANNOSIDE | − | D-ARABITOL | − |
| α-METHYL-D-GLUCOSIDE | − | L-ARABITOL | − |
| N-ACETYLGLUCOSAMINE | − | GLUCONATE | + |
| AMYGDALIN | − | 2-KETOGLUCONATE | − |
| ARBUTIN | − | 5-KETOGLUCONATE | − |
| ESCULIN | − |  |  |

*FIG. 20*

STRAIN CODE: ICP 01
IDENTIFICATION PROPOSED: PEDIOCOCCUS PENTOSACEUS
PROFILE API 50 CH

| SOURCE OF CARBON | RESPONSE |  | RESPONSE |
|---|---|---|---|
| GLYCEROL | - | SALICIN | + |
| ERYTHRITOL | - | CELLOBIOSE | + |
| D-ARABINOSE | - | MALTOSE | + |
| L-ARABINOSE | + | LACTOSE | - |
| RIBOSE | + | MELIBIOSE | - |
| D-XYLOSE | - | SACCHAROSE | - |
| L-XYLOSE | - | TREHALOSE | + |
| ADONITOL | - | INULIN | - |
| β-METHYLXYLOSIDE | - | MELEZITOSE | - |
| GALACTOSE | + | D-RAFFINOSE | - |
| D-GLUCOSE | + | STARCH | - |
| D-FRUCTOSE | + | GLYCOGEN | - |
| D-MANNOSE | + | XYLITOLE | - |
| L-SORBOSE | - | β-GENTIOBIOSE | + |
| RHAMNOSE | +V | D-TURANOSE | - |
| DULCITOL | - | D-LYXOSE | - |
| INOSITOL | - | D-TAGATOSE | + |
| MANNITOL | - | D-FUCOSE | - |
| SORBITOL | - | L-FUCOSE | - |
| α-METHYL-D-MANNOSIDE | - | D-ARABITOL | - |
| α-METHYL-D-GLUCOSIDE | - | L-ARABITOL | - |
| N-ACETYLGLUCOSAMINE | + | GLUCONATE | - |
| AMYGDALIN | + | 2-KETOGLUCONATE | - |
| ARBUTIN | + | 5-KETOGLUCONATE | - |
| ESCULIN | + |  |  |
| NB: +VE SIGNAL AN IRREGULAR RESPONSE ON THIS FEATURE (4 GALLERIES MADE AFTER SEVERAL SUCCESSIVE TRANSFERS OF THE SAME CULTURE AND CONTROL OF THE PURITY) ||||

*FIG. 29*

COMBINATIONS OF BACILLUS AND LACTOBACILLUS SPECIES FOR PRODUCING PROTEIN FROM WASTE

BACKGROUND OF THE INVENTION

1. Field of the Invention

The present invention relates to bacterial complexes which may be used in the digestion, the decomposition and the transformation of residues of biological origin in the form of biomass and of stable, non-polluting organic compounds and to their applications to the treatment of waste of biological origin, such as excrement (pig, ruminant, equid or poultry litter or human excrement, liquid manures) or liquid manures, corpses, stagnant waters and their conversion into compost or other stable, biodegradable and non-polluting nitrogenous compounds.

2. Description of the Background

Heterotrophic organisms use nitrogenous compounds, including plant or animal proteins, as nutrient sources and return the nitrogen to the soil via their excreta or via post-mortem decomposition products, mainly in the form of aqueous ammonia or urea which are converted into nitrites and nitrates by nitrifying bacteria present in the soil, such as Nitrosomonas or Nitrobacter.

However, substantial production of nitrogenous compounds in gaseous or liquid-solid form, such as ammonia gas, aqueous ammonia, nitrites and nitrates, constitutes an important cause of atmospheric pollution and of pollution of soils, water courses and water tables. All of these processes of destruction lead to the formation of compounds with particularly nauseating odours ($NH_3$ and $H_2S$ in particular, etc.).

Processes are known for the treatment of liquid manures, litters or waste waters, which involve a bacterial culture and enzymes or a bacterial culture, enzymes and yeasts, in order especially to reduce the evolution of ammonia and odours, particularly at the time of handling and during spreading (liquid manure). Such compositions contain in particular, as bacterium: *Bacillus subtilis*, as enzymes: batinase and amylase, and as yeasts: *Saccharomyces cerevisiae* (French patent application 2,658,077).

However, the compositions known for treating excrement do not allow the conversion of inorganic nitrogen ($NH_4$, $NO_2$ and $NO_3$) and urates into amino acids and proteins (organic nitrogen) but merely reduce the evolution of ammonia, by adsorption or solubilization. Such conversions do not lead to a reorganization of the nitrogen, by its use at the level of the nitrogenous metabolism of microorganisms.

Consequently, an effective treatment of products of biological origin is necessary and crucial in order to allow the conversion of inorganic nitrogen ($NH_4$, $NO_2$ and $NO_3$) and urates into organic nitrogen (amino acids and proteins), in order to prevent pollution and to return the waste into the circuit of anabolism.

SUMMARY OF THE INVENTION

In order to overcome this problem, the Applicant has selected bacterial complexes, which essentially allow the conversion of inorganic nitrogen into organic nitrogen, in the form of bacterial proteins (stabilization of the nitrogen and increase in the biomass), that is to say which allow the conversion of excrement into nitrogenous compounds (stable nitrogenous compounds and/or compost) and, particularly for waste having a sufficient C/N ratio (in relation to the level of solids content), into non-polluting compounds rich in fulvic acid and humic acid, by digestion and conversion of excrements, while at the same time removing the associated pathogenic germs, in particular Clostridium, Bacteroides, colibacilli, Listeria, salmonellae and staphylococci.

The subject of the present invention is a bacterial complex, characterized in that it essentially comprises at least one non-pathogenic Bacillus and at least one non-pathogenic Lactobacillus, in that it uses as nitrogen source essentially inorganic nitrogen, in particular aqueous ammonia, nitrates, nitrites and organic nitrogen molecules such as urea, urates, amino acids, nitrogenous bases or any other nitrogenous compound of low molecular weight, and in that it is capable of converting the said nitrogen into organic nitrogen, in the form of bacterial proteins.

BRIEF DESCRIPTION OF THE FIGURES

FIGS. 1–8: results of the API 50 CH galeries giving the fermentation profiles of sugars in Example 1;

FIGS. 9–20: results of the API 50 CH galeries giving the fermentation profiles of sugars in Example 2;

FIG. 29: results of API 50 CH galeries giving the fermentaion profiles of sugars in Example 3.

DETAILED DESCRIPTION OF THE INVENTION

Figure 21:
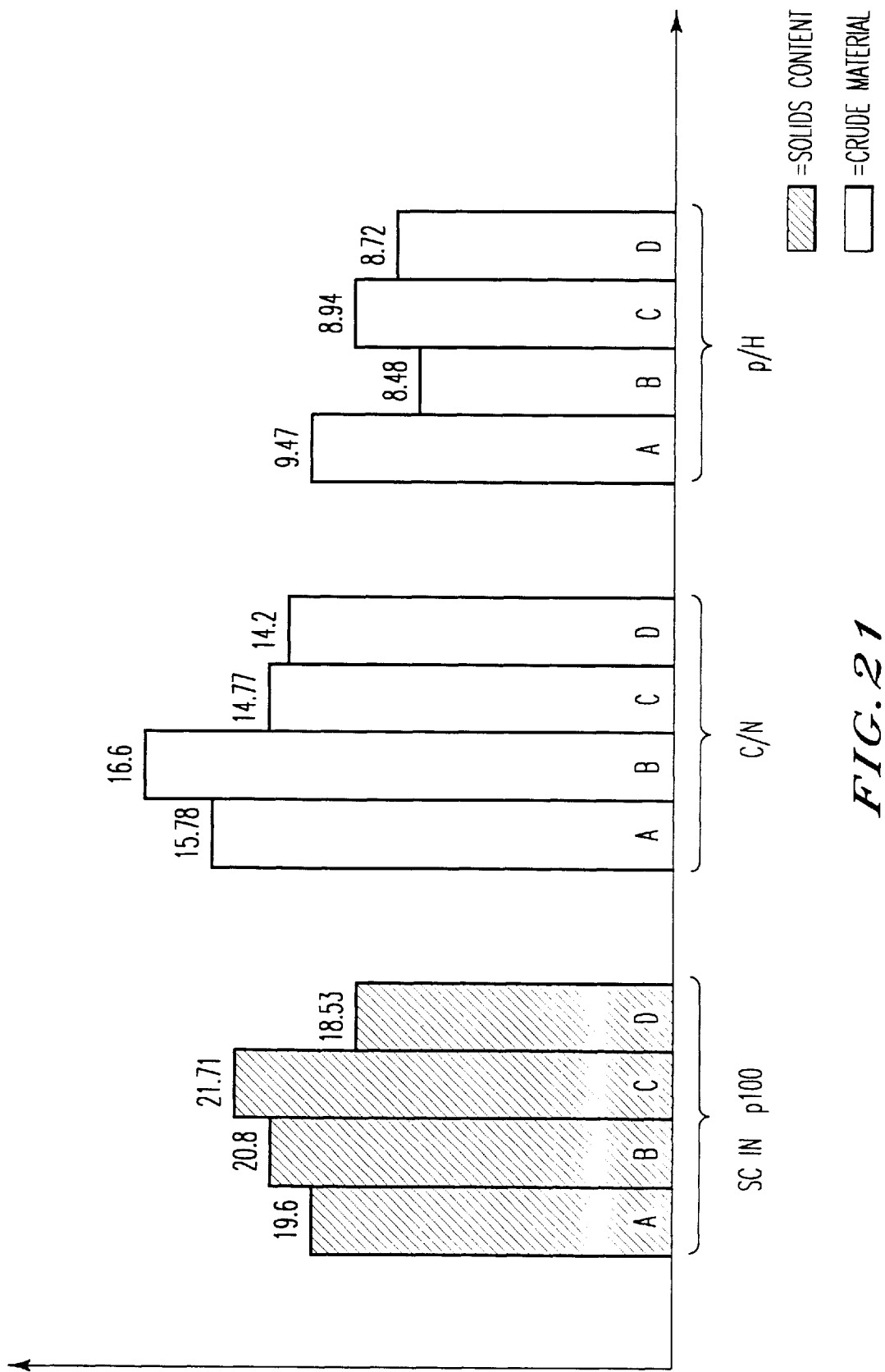
FIG. 21: results from Example 13.

In accordance with the invention, the said bacterial complex has at least the following enzymatic activities: cellulolytic activity, proteolytic activity, amylolytic activity, lipolytic activity, pectinolytic activity.

Unexpectedly, the Bacillus/Lactobacillus combination present in the bacterial complex according to the invention acts in synergy in order to:

use both inorganic nitrogen and organic nitrogen, resynthesize bacterial proteins, and remove the pathogenic microorganisms associated with the products to be treated, such as Clostridium, Bacteroides, colibacilli, Listeria, salmonellae and staphylococci.

Such a bacterial complex thus effectively makes it possible to return the waste into the circuit of anabolism (organization in the trophic chain).

According to an advantageous embodiment of the said bacterial complex, it comprises at least one Bacillus selected from the group consisting of *B. subtilis, B. amylolicuefaciens, B. megaterium, B. licheniformis* and *B. circulans* and at least one Lactobacillus selected from the group consisting of *L. rhamnosus, L. paracasei, L. fermentum* and *L. acidophilus*.

In accordance with the invention, the Lactobacillus/Bacillus proportions in the said complex are, depending on the case, either between 100/1 and 1/100, preferably between 10/1 and 1/10, or of 1/1.

In accordance with the invention, the concentrations of bacteria are between $10^2$ and $10^8$ cfu/g.

The said bacterial complex advantageously comprises at least one Bacillus, at a concentration between $10^2$ and $10^7$ cfu/g and at least one Lactobacillus, at a concentration between $10^3$ and $10^8$ cfu/g. Such a bacterial complex preferably finds application in the treatment of ruminant, equid or pig litter.

According to an advantageous arrangement of the said embodiment, the said bacterial complex comprises at least *B. subtilis* at a concentration between $10^2$ and $10^7$ cfu/g and a Lactobacillus selected from the group consisting of *L. rhamnosus, L. paracasei, L. fermentum*, and *L. acidophilus*, at a concentration between $10^3$ and $10^8$ cfu/g.

According to another advantageous arrangement of the said complex, it comprises the following 5 Bacilli: *B. subtilis, B. amyloliquefaciens, B. megaterium, B. licheniformis* and *B. circulans*, each at a concentration of between $10^2$ and $10^7$ cfu/g and the following 4 Lactobacilli: *L. rhamnosus, L. paracasei, L. fermentum, L. acidophilus*, each at a concentration of between $10^3$ and $10^8$ cfu/g.

Advantageously, when the said bacterial complex comprises several Bacilli and/or several Lactobacilli, the various strains within the same genus (Bacillus or Lactobacillus) are in a ratio of between 1:1 and 1:100.

In another embodiment of the said bacterial complex, it preferably comprises at least one Bacillus using urates as nitrogen source, in particular *B. subtilis* at a minimum concentration of $10^3$ cfu/g, optionally another Bacillus, selected from the group consisting of *B. amyloliquefaciens, B. megaterium, B. licheniformis* and *B. circulans* and at least one Lactobacillus selected from the group consisting of *L. rhamnosus, L. paracasei, L. fermentum* and *L. acidophilus* at a concentration of between $10^2$ and $10^8$ cfu/g. Such a bacterial complex is particularly well suited to the treatment of poultry litters or of the litters of other monogastric animals (with the exception of pigs).

In another embodiment of the said bacterial complex, it preferably comprises at least one Lactobacillus selected from the group consisting of *L. rhamnosus, L. paracasei, L. fermentum* and *L. acidophilus* and at least one Bacillus selected from the group consisting of *B. subtilis, B. amyloliquefaciens, B. megaterium, B. licheniformis* and *B. circulans*, the Lactobacillus/Bacillus ratio being between 1/1 and 1/10. Such a bacterial complex is particularly well suited to the treatment of septic tanks, lagoons or liquid manures.

In another embodiment of the said bacterial complex, it preferably comprises the following two Bacilli: *B. subtilis* and *B. megaterium*, each at a concentration of between $10^2$ and $10^7$ cfu/g and at least one Lactobacillus selected from the group consisting of *L. rhamnosus, L. paracasei, L. fermentum* and *L. acidophilus*, at a concentration of between $10^3$ and $10^8$ cfu/g. Such a bacterial complex is especially suitable for the treatment of animal corpses.

Surprisingly, the combination of at least one Bacillus and at least one Lactobacillus, as are defined above, effectively makes it possible to obtain a bacterial complex which:
 converts faecal or urinary residues or other waste of biological origin into bacterial proteins via bacterial synthesis, that is to say using inorganic nitrogen originating from the various wastes, either directly or by degradation;
 deodorizes manure;
 can denitrify various media and/or water;
 significantly accelerates composting, without destruction of the material and at low temperatures (below 45° C.).

Such a selection of strains does not, moreover, lead to a loss of nitrogen over time (stabilization of the level of nitrogen).

In addition, the bacterial complex in accordance with the invention is stable over time.

As a variant, the said bacterial complex comprises at least one non-pathogenic Bacillus, at least one non-pathogenic Lactobacillus and a non-pathogenic Pediococcus.

When a bacterial complex in accordance with the invention comprises a Pediococcus, the latter is at the same concentrations as the Lactobacilli.

Surprisingly, besides the properties outlined above, such a bacterial complex has an inhibitory activity with respect to *Staphylococcus aureus*.

Another subject of the present invention is Gram+Bacillus strains which can be used in a bacterial complex as defined above, characterized:
 in that they are able to use, as a source of nitrogen, inorganic nitrogen, in particular aqueous ammonia, nitrates and nitrites, and organic nitrogen molecules such as urea, urate, amino acids, nitrogenous bases or other nitrogenous compounds of low molecular weight,
 in that they have at least one of the following activities: amylolytic activity, cellulolytic activity, lignocellulolytic activity, pectinolytic activity, lipolytic activity, proteolytic activity, keratolytic activity, bacteriocin-type activity or bacteriocin-like activity,
 in that they have at least the following biochemical characteristics: gelatinase+, catalase+, urease-, oxidase-, indole- and
 in that they are preferably facultative aerobes/anaerobes.

Such Bacillus strains are preferably selected from the group consisting of *Bacillus subtilis, Bacillus amyloliquefaciens, Bacillus megaterium, Bacillus licheniformis* and *Bacillus circulans*.

The said Bacillus strains have been filed with the Collection Nationale de Cultures de Micro-organismes (CNCM) [National Collection of Microorganism Cultures], on Jun. 8, 1994, under the numbers I-1433, I-1438 and I-1440 as regards *Bacillus subtilis*, under the numbers I-1434 and I-1435 as regards *Bacillus amyloliquefaciens*, under the number I-1436 as regards *Bacillus megaterium*, under the number I-1437 as regards *Bacillus licheniformis* and under the number I-1439 as regards *Bacillus circulars*.

Another subject of the present invention is Gram+ Lactobacillus strains which can be used in a bacterial complex as defined above, characterized:
 in that they are able to use, as a source of nitrogen, inorganic nitrogen, in particular aqueous ammonia, nitrates and nitrites, and organic nitrogen molecules such as urea, urate, amino acids, nitrogenous bases or other nitrogenous compounds of low molecular weight,
 in that they have at least one bacteriocin-type activity or bacteriocin-like activity,
 in that they advantageously have at least the following biochemical characteristics: catalase-, oxidase-, and
 in that they are preferably facultative aerobes/anaerobes.

Such Lactobacillus strains are preferably selected from the group consisting of *Lactobacillus rhamnosus, Lactobacillus paracasei, Lactobacillus acidophilus* and *Lactobacillus fermentum*.

The said Lactobacillus strains have been filed with the Collection Nationale de Cultures de Micro-organismes (CNCM), on Jul. 28, 1994, under the numbers I-1450, I-1452, I-1453, I-1454, I-1455, I-1456 and I-1459 as regards *Lactobacillus rhamnosus*, under the numbers I-1451, I-1457 and I-1458 as regards *Lactobacillus paracasei*, under the number I-1460 as regards *Lactobacillus acidophilus* and under the number I-1461 as regards *Lactobacillus fermentum*.

Another subject of the present invention is Gram-positive Pediococcus strains which can be used in a bacterial complex as defined above, characterized:

in that they have a bacteriocin-type or bacteriocin-like activity at least with respect to Staphylococcus aureus, in that they advantageously have at least the following biochemical characteristics: catalase−, oxidase−, and in that they are preferably facultative aerobes/anaerobes.

A Pediococcus strain corresponding to this definition which may be mentioned in particular is the strain Pediococcus pentosaceus, filed with the Collection Nationale de Cultures de Micro-organismes (CNCM), on Dec. 22, 1995, under the number I-1654.

Unexpectedly, bacterial complexes comprising in combination at least one Bacillus and at least one Lactobacillus and optionally a Pediococcus, having the characteristics specified above, act in synergy in order for the products treated in their presence to be rendered in a useful form and thereby reduce the drawbacks, nuisance or even pollution of the said products, to sanitationally acceptable levels for soils, crops and the food chain as a whole and thus participate favourably in waste treatment.

The bacterial complex according to the invention is advantageously obtained from the said strains as follows:

culturing and production of each strain separately, production of various cultures each having microorganism concentrations of the order of $10^{10}$–$10_{11}$ cfu/g, freeze-drying of each culture, dilution, to between 1/100–1/1,000,000, of each of the said freeze-dried strains, in the presence of a neutral diluent (plant or mineral diluent such as clay, corn lithothamne-grit, etc.), and mixing together the various strains thus diluted in order to obtain the desired bacterial complex.

It may moreover comprise additives such as a chemical or microbiological tracer.

Another subject of the present invention is a composition for the treatment of biological residues (dilute, ready-to-use product), characterized in that it comprises in combination a bacterial complex in accordance with the invention, at least one neutral diluent and at least one microparticle binder.

Indeed, the bacterial complexes as defined above constitute a bacterial concentrate which may preferably be bound to a support in order to be used for the treatment of manures, liquid manures, composts, corpses, etc.

Such compositions thus advantageously comprise a neutral diluent, which is identical to or different from that used in order to prepare the bacterial complex, and a microparticle binder, such as molasses, which acts both as an energetic element and provides an effect of adhesive bonding of the particles, starch derivatives or derivatives of other sugars (complex sugars which are degraded slowly) and a coating fat or oil.

Preferably, the said composition essentially comprises 5–15% of bacterial complex, 80–89% of neutral diluent and 3–5% of microparticle binder, preferably 10% of bacterial complex, 87% of neutral diluent and 3% of particle binder.

The said treatment composition has the same applications as the bacterial complex in accordance with the invention, at lower but effective concentrations.

It may be used in particular, by direct incorporation into litters, liquid manures or any other organic product to be treated [manures, plant waste, organic waste (abattoir waste and corpses)], in proportions of 0.2 to 50 kg per ton of organic product.

In accordance with the invention, the proportions of the said incorporation vary depending on the application, in particular:

as regards litters: a bacterial complex or a treatment composition in accordance with the invention is incorporated into the litter at a rate of 10 kg/t of straw; weekly maintenance is recommended at a rate of 3 kg/t of straw;

as regards liquid manures: a bacterial complex or a treatment composition in accordance with the invention is incorporated into the liquid manures at a rate of 100 g to 1 kg/t; weekly maintenance is recommended at a rate of 100 g to 3 kg/t;

as regards manures to be composted: a bacterial complex or a treatment composition in accordance with the invention is incorporated into the manures to be composted at a rate of 1 to 5 kg/t, in a single addition;

as regards corpses to be composted: a bacterial complex or a treatment composition in accordance with the invention is incorporated with the corpses to be composted at a rate of 1 to 10 kg/t, in a single addition;

as regards lagoons, a bacterial complex or a treatment composition in accordance with the invention is incorporated into the lagoons at a rate of 500 g/m$^2$, once every 3 months;

as regards septic tanks: a bacterial complex or a treatment composition in accordance with the invention is incorporated into the septic tanks at a rate of 100 g to 1 kg/t; weekly maintenance is recommended at a rate of 100 g to 3 kg/t;

as regards the disinfection of premises and in particular the disinfection of lavatories: a bacterial complex or a treatment composition in accordance with the invention is applied in the form of a layer (artificial biofilm), to the walls and floors of the said premises, at a rate of 10 g/l of water; the solution obtained is preferably sprayed onto the said walls.

Another subject of the present invention is a process for the treatment of biological residues, such as excrement, manure, corpses or the like, characterized in that it comprises the placing in contact of a bacterial complex in accordance with the invention or of a composition as defined above with a biological residue to be treated.

Besides the preceding arrangements, the invention also comprises other arrangements, which will emerge from the following description which refers to examples of implementation of the process forming the subject of the present invention.

It should obviously be understood, however, that these examples are given solely by way of illustration of the subject of the invention, of which they in no way constitute a limitation.

EXAMPLES

Example 1

Characteristics of the Bacilli in Accordance with the Invention

The said strains exhibit the morphological and biochemical characteristics illustrated in the following tables:

| Characteristics | B. Subtilis | | | B. amyloliquefaciens | |
|---|---|---|---|---|---|
| | ISB02 | ISB09 | 1SB12 | ISB04 | ISB05 |
| Bacilli: | thin, long, | small and | long, thin, | medium size, | long and |

-continued

|  | rounded ends | bulky | often grouped in palisades | round ends | thin |
|---|---|---|---|---|---|
| Gram+ with sub-terminal spore |  | + |  | + |  |
| Recommended culture medium |  | BNG |  | BNG |  |
| mobility |  | + |  | + |  |
| Incubation time |  | 30° C. |  | 30° C. |  |
| Growth: |  |  |  |  |  |
| at 55° C. |  | + | − |  | + |
| at 10° C. |  | − |  |  | − |
| Growth |  |  |  |  |  |
| at 2% NaCl |  | +++ | +++ |  | +++ |
| at 5% NaCl |  | +++ | +++ |  | +++ |
| at 7% NaCl |  | ++ | +++ | ++ | +++ |
| at 10% NaCl |  | − | + | − | + |
| Citrate |  | + |  |  | − |
| Gelatinase |  | + |  |  | + |
| Nitrate |  | + |  | + | − |
| $N_2$ |  | + | − |  | − |
| Glucose fermentation |  |  | − |  | − |
| Catalase |  | + |  |  | + |
| Oxidase |  | − |  |  | − |
| Urease |  | − |  |  | − |
| ONPG |  | + |  |  | + |
| Indole |  | − |  |  | − |
| Casein |  | + | + |  | + |
| Acetoin |  | + |  |  | + |
| ADH |  | + | − | + | − |

| Characteristics | B. megaterium ISB06 | B. licheniformis ISB07 | B. circulans ISB11 |
|---|---|---|---|
| Bacilli: | medium, with round ends | medium | medium, round ends, fairly bulky |
| Gram+ with sub-terminal spore | + | + | + |
| Recommended culture medium | BNG | BNG | BNG |
| mobility | + | + | + |
| Incubation time | 30° C. | 30° C. | 30° C. |
| Growth: |  |  |  |
| at 55° C. | + | − | − |
| at 10° C. | − | − | + |
| at 2% NaCl | +++ | +++ | ++ |
| at 5% NaCl | +++ | +++ | + |
| at 7% NaCl | +++ | ++ | − |
| at 10% NaCl | + | − | − |
| Citrate | + | − | − |
| Gelatinase | + | + | + |
| Nitrate | + | + | − |
| $N_2$ | − | − | − |
| Glucose fermentation | − | + | − |
| Catalase | + | + | + |
| Oxidase | − | − | − |
| Urease | − | − | − |
| ONPG | + | + | − |
| Indole | − | − | − |
| Casein | + | + | − |
| Acetoin | − | + | − |
| ADH | − | + | − |

The results of the API 50 CH galeries giving the fermentation profile of sugars (positive features after maximum incubation of 48 h) (inoculation according to API) (point 2 on the MacFarland scale) are illustrated in FIGS. 1 to 8.

Example 2
Characteristics of the Lactobacilli in Accordance with the Invention The said strains have the morphological and biochemical characteristics illustrated in the following tables:

| Characteristics | Lactobacillus rhamnosus | | |
|---|---|---|---|
|  | ISL01 | ISL05 | ISL10 |
| Rods | fairly long, not sporulated, sometimes in small chains | not sporulated, medium size, sometimes in small chains | not sporulated, medium to long size, some in small chains |
| Gram+ | + | + | + |
| Recommended culture medium | MRS or Rogosa | MRS or Rogosa | MRS or Rogosa |
| Mobility | − | − | − |
| Incubation time | 30° C. | 37° C. | 37° C. |
| Growth: |  |  |  |
| at 15° C. | + | + | + |
| at 45° C. | + | + | + |
| Glucose fermentation | homofermentational | homofermentational | homofermentational |
| Catalase | − | − | − |
| Oxidase | − | − | − |

| Characteristic | Lactobacillus rhamnosus | | | |
|---|---|---|---|---|
|  | ISL20 | ISL21 | ISL25 | ISL35 |
| Rods | not sporulated, medium size sometimes in chains | not sporulated, medium size | not sporulated, sometimes in chains | not sporulated, medium size |
| Gram+ | + | + | + | + |
| Recommended culture medium | MRS or Rogoso | MRS or Rogoso | MRS or Rogoso | MRS or Rogoso |
| Mobility | − | − | − | − |
| Incubation time | 37° C. | 37° C. | 37° C. | 37° C. |
| Growth: |  |  |  |  |
| at 15° C. | + | + | + | + |
| at 45° C. | + | + | + | + |
| Glucose fermentation | homofermentational | homofermentational | homofermentational | homofermentational |
| Catalase | − | − | − | − |
| Oxidase | − | − | − | − |

| Characteristics | Lactobacillus paracasei | | |
|---|---|---|---|
|  | ISL03 | ISL27 | ISL32 |
| Rods | uniform, not sporulated, of medium size | long, not sporulated | not sporulated, of medium size |
| Gram+ | + | + | + |
| Recommended culture medium | MRS | MRS or Rogosa | MRS or Rogosa |
| Mobility | − | − | − |
| Incubation time | 30° C. | 30° C. | 30° C. |
| Growth: |  |  |  |
| at 15° C. | + | + | + |
| at 45° C. | + | + | + |
| Glucose fermentation | homofermentational | homofermentational | homofermentational |
| Catalase | − | − | − |
| Oxidase | − | − | − |

| Characteristics | Lactobacillus acidophilus ISL44 | Lactobacillus fementum ISL102 |
|---|---|---|
| Rods | not sporulated, fairly long, sometimes in small chains | medium, not sporulated, sometimes in pairs |
| Gram+ | + | + |
| Recommended culture medium | MRS or Rogosa | MRS or Rogosa |
| Mobility | − | − |
| Incubation time | 30° C. | 37° C. |
| Growth: |  |  |

-continued

| | | |
|---|---|---|
| at 15° C. | − | − |
| at 45° C. | − | + |
| Glucose fermentation | homofermentational | heterofermentational |
| Catalase | − | − |
| Oxidase | − | − |

The results of the API 50 CH galeries giving the fermentation profile of sugars (positive features after maximum incubation of 48 h) (inoculation according to API) are illustrated in FIGS. 9 to 20.

Example 3

Characteristics of the Pediococci in Accordance with the Invention

The strain of Pediococcus pentosaceus has the morphological and biochemical characteristics illustrated in the following table:

| Characteristics | Pediococcus pentosaceus ICP01 |
|---|---|
| Cocci | In pairs, or less frequently, in tetrads; never in small chains |
| Gram+ | + |
| Recommended culture medium | MRS |
| Incubation time | 37° C. |
| Growth: | |
| at 15° C. | − |
| at 45° C. | + |
| at pH 8 | + |
| at 4% NaCl | + |
| at 6.5% NaCl | + |
| at 15% NaCl | − |
| Glucose fermentation | homofermentational |
| Catalase | − |
| Oxidase | − |
| Arginine | + |
| Nitrate | − |
| ONPG | − |
| Indole | − |
| Acetone | − |

The results of the API 50 CH galeries giving the fermentation profile of sugars (positive features after maximum incubation of 48 h) (inoculation according to API) are illustrated in FIG. 29.

Example 4

Activities of the Bacilli and Lactobacilli

The selection of strains having an enzymatic activity in particular allows a controlled digestion of excrement.

1) Enzymatic activities

Proteolytic activity:

For the majority of the tests, the enzymatic activities are demonstrated on the basic minimum medium (BMM), based on agar, for the Bacillus strains, and on Rogosa medium for the Lactobacillus strains.

The strains are seeded in stripes onto the BMM medium or the Rogosa medium, both of which are supplemented with 1% (weight/volume) of powdered skimmed milk, rich in casein which is liable to be hydrolysed.

After an incubation of 24 hours in the oven at 30° C. for the Bacilli and of 5 days in an anaerobic oven at 37° C. for the lactic flora, the presence of proteolytic activity is reflected in clarification of the medium, due to hydrolysis of the casein.

Amylolytic activity:

As above, the bacterial strains are seeded in stripes onto the two media supplemented with 1% (weight/volume) of insoluble wheat starch. After incubation under the same conditions as above, the amylolytic activity is reflected in clarification of the medium around the colonies arranged in stripes, due to hydrolysis of the starch.

Cellulolytic activity:

The procedure is the same as for the investigation of the amylolytic activity. The carbon-containing substrate used is carboxymethylcellulose.

Hydrolysis of uric acid:

The principle is the same as for the degradation of starch, the uric acid being added at a concentration of 1% (weight/volume); hydrolysis of the uric acid is reflected in clarification of the medium.

The table below illustrates the results and the reaction products obtained:

| | Presence of urea | Urease | Presence of aqueous ammonia |
|---|---|---|---|
| B. subtilis (ISB02) | +/− | +/− | +/− |
| B. amyloliquefaciens (ISB04) | − | − | ++ |
| B. amyloliquefaciens (ISB05) | +/− | +− | ++ |
| B. megaterium (ISB06) | − | − | ++ |
| B. licheniformis (ISB07) | − | +/− | ++ |
| B. subtilis (ISB09) | − | + | + |
| B. circulans (ISB11) | − | − | − |
| B. subtilis (ISB12) | − | − | +/− |

These results show that, with the exception of the strain ISB11, all of the Bacilli are capable of degrading uric acid to aqueous ammonia.

Hydrolysis of urea:

The hydrolysis of urea is visualized using Stuart's medium. This medium contains a coloured indicator: phenol red, which changes from yellow to deep pink throughout the tube when the urea is hydrolysed.

Lipolytic activity:

The various strains are seeded on a tributyrine agar medium. Before use, the media, distributed in tubes, are stirred so as to emulsify the tributyrine, and are then poured into Petri dishes. After incubation under the conditions specified above, hydrolysis of the tributyrine is visualized by lightening of the medium around the colony.

The table below illustrates the various activities specified above.

Bacillus

| Code | NO$_3$ | NO$_2$ | Urea | Amiolytic activity | Proteolytic activity | Lipolytic activity | 55° C. | 60° C. | Facultative anaerobic/ aerobic |
|---|---|---|---|---|---|---|---|---|---|
| ISB02 | + | – | + | + | + | + | + | + | + |
| ISB04 | + | – | – | + | + | + | – | – | + |
| ISB05 | + | – | – | + | + | + | – | – | + |
| ISB06 | + | – | – | + | + | + | – | – | + |
| ISB07 | + | – | – | + | + | + | – | – | + |
| ISB09 | + | – | – | + | + | + | – | – | + |
| ISB11 | | – | | + | +/– | +/– | | | – |
| ISB12 | | – | | + | + | + | | | – |

The various bacilli also have other enzymatic activities listed in the table below:

| Enzymatic activities | Xylanase | CMcase | Cellulase | Keratinase | Pectinase |
|---|---|---|---|---|---|
| *B. subtilis* (ISB02) | + | + | – | ++ | + |
| *B. amylolique-faciens* (ISB04) | + | + | +/– | + | + |
| *B. amylolique-faciens* (ISB05) | + | + | – | – | ++ |
| *B. megaterium* (ISB06) | + | + | +/– | – | + |
| *B. licheni-formis* (ISB07) | + | + | – | – | +/– |
| *B. subtilis* (ISB09) | + | + | +/– | – | + |
| *B. circulans* (ISB11) | + | + | ++ | – | – |
| *B. subtilis* (ISB12) | + | + | +/– | – | – |

The lactobacilli selected have no amylolytic, proteolytic or lipolytic activity.

2) Bacteriocin-type and Bacteriocin-like Activity:

The search for inhibitory substances is carried out for all the strains selected.

The bacteriocins are proteins of plasmidic origin, the particular feature of which is to have a bactericidal activity, directed against bacteria from the same species or from homologous species. The strains producing bacteriocins possess a gene for immunity towards their own bacteriocin. The expression bacteriocin-like activity is used for the bactericidal activities directed against the heterologous bacteria.

Strains capable of producing inhibitory substances of bacteriocin type are selected by observation, in a Petri dish, of lightening around a bacterial colony. This lightening corresponds to inhibition of the pathogenic bacteria present in the agar by the strains selected.

The pathogenic bacteria used for this investigation are:

*Escherichia coli* (serotype 078K82)

*Salmonella enteritidis*

*Salmonella typhimurium*

*Staphylococcus aureus*

*Clostridium perfringens*

*Clostridium septicum*

*Listeria monocytogenes.*

These are the main pathogens encountered in contaminated litters.

The media used for culturing the pathogenic bacteria are listed in the table below.

Culture Media for Pathogenic Bacteria

| Strains | Liquid medium | Agar medium |
|---|---|---|
| *Escherichia coli* | BNL | BNG |
| *Staphylococcus aureus* | BNL | BNG |
| Salmonella | BNL | BNG |
| Clostridium | RCM broth | RCM agar |
| Listeria | Tryptose | agar tryptose | the Lactobacilli produce lactic acid, which is the main source of in vitro inhibition of the pathogenic bacteria.

In order to neutralize this factor, Rogosa medium buffered to pH 6.1 with a phosphate buffer is used to culture the Lactobacilli.

After seeding of the various Lactobacillus strains and incubation, for 8 h at 37° C. under anaerobiosis, each colony is covered with one drop of medium specific for the pathogenic bacterium to be tested.

20 ml of agar medium of the specific pathogenic strains supplemented with 5 ml of a pathogenic bacterial culture are poured into the dish.

The Petri dishes are read after incubation for 24 h at 37° C.

The size of the inhibition zones produced is measured; the inhibition diameter calculated corresponds to the difference between the diameter of the inhibition zone and the diameter of the Lactobacillus colony. The results are illustrated in the table below.

Lactobacillus

| Code | *S. enteritidis* | *S. typhimurium* | *E. coli* K82 | Listeria ½ a | Listeria ½ b | Listeria ½ c |
|---|---|---|---|---|---|---|
| ISL01 | 9 | 6 | 8 | 9 | 11 | 8 |
| ISL03 | 15 | 8 | 9 | – | – | – |
| ISL05 | 6 | 4 | 2 | – | 15 | 15 |
| ISL10 | 7 | 8 | 8 | – | 13 | 11 |
| ISL20 | – | – | 2 | 8 | 23 | 15 |
| ISL21 | – | – | 18 | – | 9 | – |
| ISL25 | 7 | 8 | – | – | 16 | – |
| ISL27 | 10 | 12 | 12 | – | – | – |
| ISL32 | 8 | – | 8 | – | 18 | 15 |
| ISL35 | 10 | 5 | 5 | – | 12 | 22 |
| ISL44 | 12 | 5 | 6 | 7 | 6 | 8 |
| ISL102 | 8 | 0 | 0 | 8 | 0 | 10 |

In order to study the bacteriocin action of the Bacilli, the conditions are as follows:

10 ml of PCA medium are poured into Petri dishes; 24-hour-old cultures of the Bacillus strains selected are spot-plated; after incubation for 24 h at 30° C., the agar is loosened with a sterile spatula and turned out into a Petri dish 9 cm in diameter; 20 ml of agar medium specific for the pathogenic strains, supplemented with 5 ml of a preculture of these same bacteria, are poured into the Petri dish.

The Petri dishes are read after incubation for 24 h, as specified above for the Lactobacilli.

The table below illustrates the results obtained.

Bacillus

| Code | Clostridium perfringens Ø mm | Clostridium septicum Ø mm | E. coli 078K82 Ø mm | Salmonella enteritidis Ø mm | Salmonella typhimurium Ø mm | Listeria |
|---|---|---|---|---|---|---|
| ISB2 | 13 | 0 | 0 | 0 | 0 | 0 |
| ISB4 | 19 | 9 | 2 | 2 | 7 | 0 |
| ISB5 | 20 | 22 | 8 | 8 | 4 | 0 |
| ISB6 | 12 | 8 | 5 | 7 | 5 | 0 |
| ISB7 | 9 | 12 | 4 | 8 | 6 | 0 |
| ISB9 | 18 | 11 | 0 | 0 | 0 | 0 |
| ISB11 | 0 | 0 | 0 | 0 | 0 | 0 |
| ISB12 | 10 | 0 | 0 | 0 | 0 | 14 |

None of the strains selected exhibits an inhibitory activity with respect to *Staphylococcus aureus*. On the other hand, these various strains selected have particularly advantageous inhibition spectra as well as all of the desired enzymatic activities.

3) MIC of Various Growth Factors:

a) Bacillus:

| Growth factor (µg/ml) code | flavomycin | tylan | stafac | sacox | monensin | avotan | spiramycin |
|---|---|---|---|---|---|---|---|
| B. subtilis (ISB02) | >10 | 2.5 | 5 | 2.5 | >10 | <0.625 | >10 |
| B. amyloliquefaciens (ISB04) | >10 | 5 | >10 | 1.25 | >10 | <0.625 | 10 |
| B. amyloliquefaciens (ISB05) | >10 | <0.625 | 5 | 2.5 | >10 | <0.625 | 10 |
| B. megaterium (ISB06) | 10 | 2.5 | 10–5 | 2.5 | >10 | <0.625 | 10 |
| B. licheniformis (ISB07) | >10 | 2.5 | >10 | 2.5 | >10 | <0.625 | 2.5 |
| B. subtilis (ISB09) | 10 | 2.5 | 5–2.5 | 2.5 | 10 | <0.625 | 10 |
| B. circulans (ISB11) | <0.625 | 1.25 | 1.25 | <0.625 | >10 | <0.625 | 5 |
| B. subtilis (ISB12) | >10 | 10–5 | 10 | 1.25 | >10 | <0.625 | 10 | b) Lactobacillus:

| Growth factor (μg/ml) code | flavomycin | tylan | stafac | sacox | monensin | avotan | spiramycin |
|---|---|---|---|---|---|---|---|
| L. rhamnosus (ISL01) | 5–2.5 | <2.5 | <2.5 | 2–1 | <2.5 | 40–20 | <5 |
| L. paracasei (ISL03) | 10–5 | <2.5 | <2.5 | 4–2 | 20–10 | R | <5 |
| L. rhamnosus (ISL05) | 40–20 | <2.5 | 5–2.5 | 2–1 | 5–2.5 | R | <5 |
| L. rhamnosus (ISL10) | 10–5 | <2.5 | 5–2.5 | 2–1 | 5–2.5 | R | <5 |
| L. rhamnosus (ISL20) | 20–10 | <2.5 | <2.5 | <1 | 20–10 | R | R |
| L. rhamnosus (ISL21) | 10–5 | <2.5 | <2.5 | <1 | 20–10 | R | <5 |
| L. rhamnosus (ISL25) | 20–10 | <2.5 | <2.5 | 4–2 | 5–2.5 | R | <5 |
| L. paracasei (ISL27) | 10–5 | <2.5 | <2.5 | 4–2 | 5–2.5 | R | <5 |
| L. paracasei (ISL32) | R | <2.5 | 20–10 | R | R | R | <5 |
| L. rhamnosus (ISL35) | R | <2.5 | 10–5 | 16–8 | 40–20 | R | <5 |
| L. acidophilus (ISL44) | 40–20 | 20–10 | 40–10 | R | R | R | 20–10 |
| L. fermentum (ISL102) | R | <2.5 | 10–5 | 8–4 | 40–20 | R | <5 |

These results show that the Lactobacillus strains tested are more resistant than the Bacillus strains; strong inhibition of the Bacillus strains by avotan and sacox is noted, the respective MICs being <0.625 and 1.25.

The strain of ISL44 is resistant to the majority of the growth factors.

Example 5

Bacteriocin-type and Bacteriocin-like Activity of Pediococcus pentosaceus.

After culturing Pediococcus on MRS medium (de Man, Rogosa and Sharpe) containing 4% NaCl, a range of suspension-dilutions down to $10^{-7}$ is made; the dilutions $10^{-1}$ to $10^{-5}$ are seeded on the surface on Petri dishes containing the MRS medium, at a rate of 0.1 ml per dilution, and are then spread out with a rake. The seedings are done in duplicate for each dilution. The dishes are incubated at 37° C. for 48 h in an anaerobic oven (10% $CO_2$ and 90% $N_2$).

Before recovering the culture supernatant, the purity of the strain is controlled by seeding the strains on MRS agar dishes, according to the quadrant technique (culture for 48 h at 37° C. in an anaerobic oven). A correctly isolated colony makes it possible to inoculate a tube of 10 ml of MRS broth, which is then placed in the oven for 24 h at 37° C. under anaerobiosis. 1 ml of each preculture is seeded in 50 ml of MRS broth and the incubation is carried out for 16 h under the same conditions; 20 ml of culture supernatant are withdrawn at the end of the 16 h of incubation and are centrifuged at 10,000 g. The supernatant freed of the cells and containing the excreted products is recovered.

Preparation of the various controls.

Several treatments are carried out on the supernatant obtained in order to ensure that the inhibition is indeed due to the presence of a bacteriocin; indeed, the supernatant is of acidic pH (about 4.5) and contains organic acids produced by the said strain (acetic acid and lactic acid), and hydrogen peroxide (absence of catalase);

inhibition of the action of the pH: Neutralization to pH 6.5–7.5 (pH test);

evaluation of the action of the organic acids: control only containing these acids (acid test);

inhibition of the action of hydrogen peroxide: controls with catalase (incubation of 0.5 ml of catalase with 0.5 ml of Pediococcus pentosaceus culture supernatant for 1 hour at 37° C., followed by cooling for 1 hour at room temperature, before carrying out the inhibition test) (catalase test);

evaluation of the action of temperature (heat or cold) (cold and heat tests);

evaluation of the action of proteolytic enzymes (trypsin, α-chymotrypsin, pronase E), according to a procedure identical to that used for catalase (trypsin test, pronase test and α-chymotrypsin test);

evaluation of the molecular weight of the bacteriocin being produced (dialysis test).

Test of Inhibition of S. aureus

All the samples prepared (culture supernatant various controls) are sterilized using 0.2 μm filters; the test is carried out as follows:

100 ml of BNG, maintained at 45° C. and to which was added 0.5 ml of a 16-h-old culture of S. aureus, are poured into two 100 ml Petri dishes. The mixture is left to solidify; using a carrier rack, 9 wells are made in each dish. The dishes are again left to solidify for about 1 h at 4° C. Each well is then filled 100 μl of sample (culture supernatant on control), as illustrated in the table below.

| Well No. | Petri dish I | Petri dish II |
|---|---|---|
| 1 | control supernatant | control supernatant |
| 2 | catalase test | cold test |
| 3 | control catalase test* | heat test |
| 4 | trypsin test | pH test |
| 5 | pronase E test | acid test |
| 6 | control pronase E test* | dialysis test |
| 7 | control trypsin test* | buffer test only |
| 8 | α-chymotrypsin test | nothing |
| 9 | control α-chymotrypsin test* | nothing |

-continued

| Well No. | Petri dish I | Petri dish II |
|---|---|---|

*without culture supernatant

The dishes are placed at 4° C. for about 2 hours, in order for the bacteriocin to diffuse into the agar, then the entire system is placed in the oven at 37° C. for 24 h.

Results
The table below illustrates the results obtained.

| Well No. | Inhibition diameter Dish I | Inhibition diameter Dish II |
|---|---|---|
| 1 | 13 | 12 |
| 2 | 11 | 11 |
| 3 | 0 | 6 |
| 4 | 12 | 11 |
| 5 | 10 | 0 |
| 6 | 0 | 11 |
| 7 | 0 | 0 |
| 8 | 12 | 0 |
| 9 | 0 | 0 |

These results show that *Pediococcus pentosaceus* produces a bacteriocin which is effectively active on *S. aureus*.

Example 6

Demonstration of the Synergy of Action between Bacilli and Lactobacilli in a bacterial complex according to the invention 1) Comparison of the generation time (Tg), the number of cfu/ml and the survival rate for a few strains of Lactobacillus in monoculture/to their association in a bacterial complex according to the invention (on a medium consisting of sterile droppings seeded with the bacteria mentioned):

| Lactobacillus strains | Tg (h) | cfu/ml (final) | survival rate (%) |
|---|---|---|---|
| L. rhamnosus (ISL01) | 13 | $3.30 \times 10^7$ | 22.4 |
| L. rhamnosus (ISL01) + B. subtilis (ISB02) | 6 | $6.40 \times 10^7$ | 52.4 |
| L. rhamnosus (ISL01) + B. megaterium (ISB06) | 8 | $1.20 \times 10^7$ | 50.0 |
| L. rhamnosus (ISL01) + B. subtilis (ISB09) | 8 | $5.40 \times 10^6$ | 23.7 |
| L. rhamnosus (ISL21) | 9.8 | $1.00 \times 10^8$ | 100 |
| L. rhamnosus (ISL21) + B. circulans (ISB11) | 4 | $2.01 \times 10^7$ | 79.7 |

2) Comparison of the generation time and the number of ctu/ml for Bacillus strains in monoculture and in coculture:

| Bacillus strains | Tg (h) | cfu/ml max. before sporulation |
|---|---|---|
| B. megaterium (ISB06) | 2.9 | $7.3 \times 10^8$ |
| B. megaterium (ISB06) + L. paracasei (ISL27) | 0.8 | $1.20 \times 10^8$ |
| B. circulans (ISB11) | 3.2 | |
| B. circulans (ISB11) | +0.28 | $2.40 \times 10^8$ |
| L. rhamnosus (ISL21) | | |

3) Degradation of uric acid

| | 24 h (%) | 48 h (%) |
|---|---|---|
| Control | 0 | 0 |
| L. paracasei (ISL27) | 60 | 71 |
| B. megaterium (ISB06) + L. paracasei (ISL27) (with glucose) | 75 | 91 |
| L. rhamnosus (ISL21) | 48 | 63 |
| B. circulans (ISB11) + L. rhamnosus (ISL21) (with glucose) | 72 | 85 |

Example 7

Bacterial Complex for Ruminant and Pig Litter

| | Complex 1 (cfu/g) | Complex 2 (cfu/g) | Complex 3 (cfu/g) | Complex 4 (cfu/g) |
|---|---|---|---|---|
| B. subtilis | ISB02 $10^2$ | ISB02 $10^4$ | ISB02 $10^4$ | ISB02 $10^5$ |
| B. amyloliquifaciens | ISB05 $10^2$ | ISB05 $10^4$ | ISB05 $10^4$ | ISB05 $10^5$ |
| B. megaterium | ISB06 $10^2$ | ISB06 $10^4$ | ISB06 $10^4$ | ISB06 $10^5$ |
| B. licheniformis | ISB07 $10^2$ | ISB07 $10^4$ | ISB07 $10^4$ | ISB07 $10^5$ |
| B. circulans | ISB11 $10^2$ | ISB11 $10^4$ | ISB11 $10^4$ | ISB11 $10^5$ |
| L. rhamnosus | ISL20 $10^3$ | ISL20 $10^4$ | ISL20 $10^5$ | ISL20 $10^6$ |
| L. paracasei | ISL32 $10^3$ | ISL32 $10^4$ | ISL32 $10^5$ | ISL32 $10^6$ |
| L. fermentum | ISL102 $10^3$ | ISL102 $10^4$ | ISL102 $10^5$ | ISL102 $10^6$ |
| L. acidophilus | ISL44 $10^3$ | ISL44 $10^4$ | ISL44 $10^5$ | ISL44 $10^6$ |

Example 8

Bacterial Complex for Poultry Litters

| | Complex 5 (cfu/g) | Complex 6 (cfu/g) | Complex 7 (cfu/g) |
|---|---|---|---|
| B. subtilis | ISB02 $10^3$ | ISB02 $10^5$ | ISB02 $10^6$ |
| B. circulans | ISB11 $10^3$ | ISB11 $10^5$ | ISB11 $10^6$ |
| L. rhamnosus | ISL20 $10^2$ | ISL20 $10^4$ | ISL20 $10^5$ |
| L. paracasei | ISL32 $10^2$ | ISL32 $10^4$ | ISL32 $10^5$ |
| L. fermentum | ISL102 $10^2$ | ISL102 $10^4$ | ISL102 $10^5$ |
| L. acidophilus | ISL44 $10^2$ | ISL44 $10^4$ | ISL44 $10^5$ |

Example 9

Bacterial Complex for Liquid Manures and for Septic Tanks

|  | Complex 8 (cfu/g) | Complex 9 (cfu/g) | Complex 10 (cfu/g) |
|---|---|---|---|
| B. subtilis | ISB02  $10^3$ | ISB02  $10^6$ | ISB02  $10^2$ |
| B. amyloliquefaciens | ISB04  $10^3$ | ISB04  $10^6$ | – |
| B. megaterium | ISB06  $10^3$ | ISB06  $10^6$ | – |
| B. licheniformis | ISB07  $10^3$ | ISB07  $10^6$ | – |
| B. circulans | ISB11  $10^3$ | ISB11  $10^6$ | ISB11  $10^2$ |
| L. rhamnosus | ISL20  $10^2$ | ISL20  $10^5$ | – |
| L. paracasei | ISL32  $10^2$ | ISL32  $10^5$ | – |
| L. fermentum | ISL102  $10^2$ | ISL102  $10^5$ | – |
| L. acidophilus | ISL44  $10^2$ | ISL44  $10^5$ | ISL44  $10^2$ |

Example 10

Bacterial Complex for Manure (Compost)

|  | Complex 11 (cfu/g) | Complex 12 (cfu/g) | Complex 13 (cfu/g) |
|---|---|---|---|
| B. subtilis | ISB02  $10^3$ | ISB02  $10^2$ | ISB02  $10^4$ |
|  | ISB12  $10^3$ | ISB04  $10^2$ | ISB04  $10^4$ |
| B. amyloliquefaciens | ISB05  $10^3$ | ISB06  $10^2$ | ISB06  $10^4$ |
| B. megaterium | ISB06  $10^3$ | ISB07  $10^2$ | ISB07  $10^4$ |
| B. circulans | ISB11  $10^3$ | ISB11  $10^2$ | ISB11  $10^4$ |
| L. rhamnosus | ISL35  $10^4$ | ISL20  $10^4$ | ISL20  $10^6$ |
| L. paracasei | ISL32  $10^4$ | ISL20  $10^4$ | ISL20  $10^6$ |
| L. fermentum | ISL102  $10^4$ | ISL102  $10^4$ | ISL102  $10^6$ |
| L. acidophilus | ISL44  $10^4$ | ISL44  $10^4$ | ISL44  $10^6$ |

Example 11

Bacterial Complex for Cleaning Lagoons

|  | Complex 14 (cfu/g) | Complex 15 (cfu/g) |
|---|---|---|
| B. subtilis | ISB02  $10^3$ | ISB02  $10^6$ |
| B. amyloliquefaciens | ISB04  $10^3$ | ISB04  $10^6$ |
| B. licheniformis | ISB07  $10^3$ | ISB07  $10^6$ |
| B. circulans | ISB11  $10^3$ | ISB11  $10^6$ |
| L. rhamnosus | ISL01  $10^2$ | ISL01  $10^5$ |
| L. paracasei | ISL03  $10^2$ | ISL03  $10^5$ |
| L. fermentum | ISL102  $10^2$ | ISL102  $10^5$ |
| L. acidophilus | ISL44  $10^2$ | ISL44  $10^5$ |

Example 12

Bacterial Complex for Treating Animal Corpses

|  | Complex 16 (cfu/g) | Complex 17 (cfu/g) | Complex 18 (cfu/g) |
|---|---|---|---|
| B. subtilis | ISB02  $10^2$ | ISB02  $10^5$ | ISB02  $10^5$ |
| B. amyloliquefaciens |  | ISB05  $10^5$ | ISB05  $10^5$ |
| B. megaterium | ISB05  $10^2$ | ISB06  $10^5$ | ISB06  $10^5$ |
| B. licheniformis |  | ISB07  $10^5$ | ISB07  $10^5$ |
| B. circulans |  | ISB11  $10^5$ | ISB11  $10^5$ |
| L. rhamnosus | ISL35  $10^3$ | ISL35  $10^5$ | ISL35  $10^6$ |
| L. paracasei | ISL32  $10^3$ or | ISL32  $10^5$ | ISL32  $10^6$ |
| L. fermentum | ISL102  $10^3$ or | ISL102  $10^5$ | ISL102  $10^6$ |
| L. acidophilus | ISL44  $10^3$ or | ISL44  $10^5$ | ISL44  $10^6$ |

Example 13

Treated/Untreated Litter Comparison a) Seeding of the litters:

The litters are seeded such that the concentration of Bacillus is 100 cfu/g of straw ($2 \times 10^3$ cfu of Bacillus per 20 g of product for treatment of litter (treatment composition or complex in accordance with the invention)).

Two different experimental methods for seeding the litters were used.

A first method consists in seeding a bacterial complex in accordance with the invention with 400 g of litter placed in a hermetically closed box. The incubation is carried out at 30° C. After 3 and 7 days of incubation, 20 g of litter are removed. The samples are then prepared as follows:

20 g of product to be analysed are mixed with 180 ml of tryptone salt diluent and are then homogenized in a Stomacher machine (Lab. Blender) for 2 min. Using this stock suspension (→dilution to ¹/₁₀th) a range of dilutions is prepared in order to perform the microbial analysis.

In the second method used, in order to improve the homogeneity of the seedings, 20 g of litter are placed in a Stomacher bag with filter, which prevents litter residues from being withdrawn during the dilutions. The seeding is performed directly in the bags, which are incubated for the desired time at 30° C., each time corresponding to a bag. 60 ml of tryptone-salt diluent are next mixed with the litter, then a range of decimal dilutions is prepared.

The following are counted:

the heat-resistant flora (Bacillus)

the faecal coliforms, the sulphito-reducing anaerobes (Clostridium), the lactic flora (Lactobacillus), in accordance with the usual culture procedures.

Figure 23:
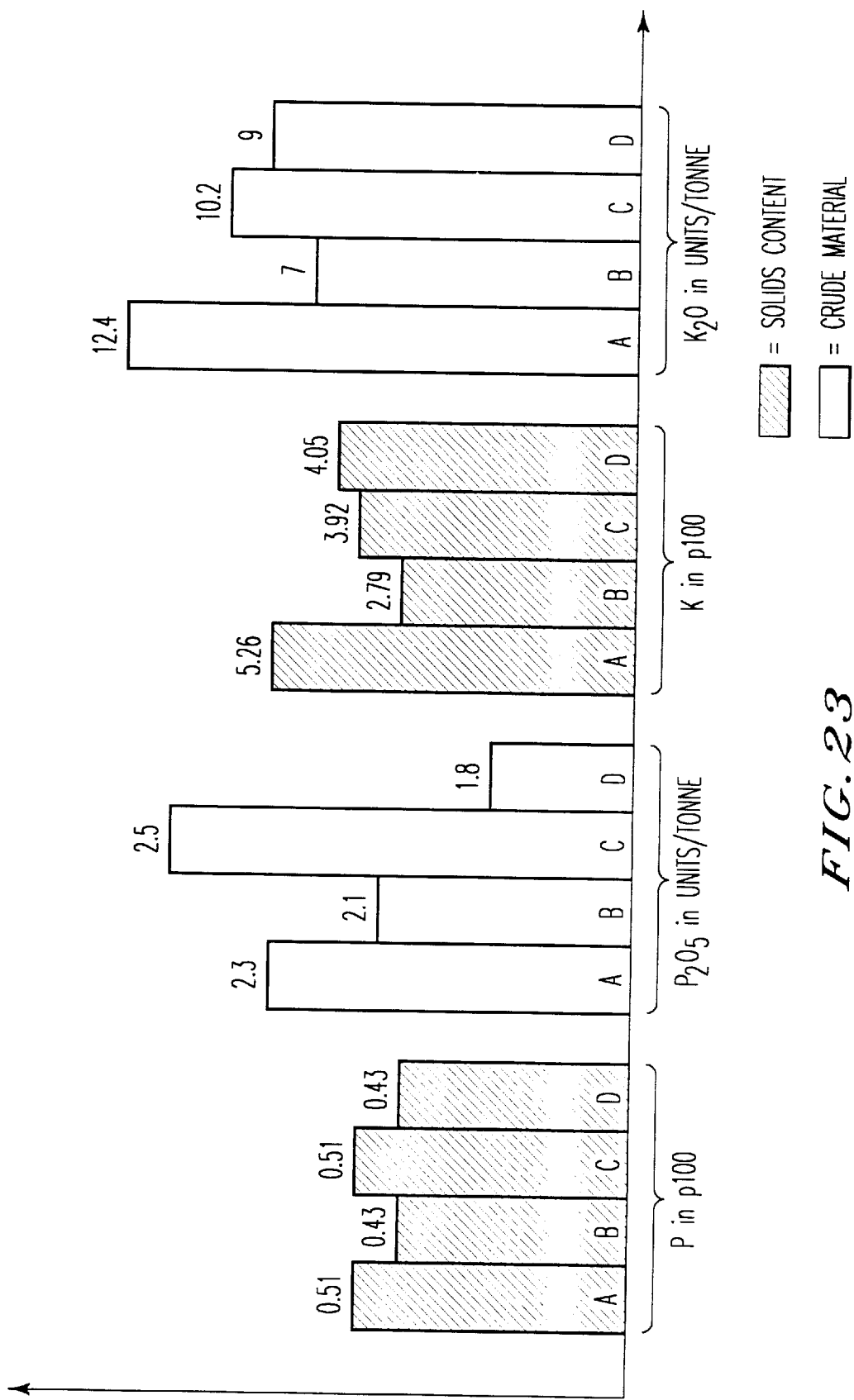
FIG. 23: results from Example 13.

The presence of Salmonella is also investigated.

b) Change in the nitrogen (solubility, ammoniacal nitrogen, amino nitrogen) and in the solids content of litter treated with a complex according to the invention (cattle litter according to Example 4):

FIGS. 21 and 23 show the change over time of the solids content (as a percentage), the C/N ratio, the pH, the total nitrogen (as a percentage), the solubility of nitrogen (as a percentage), the percentage of ammoniacal nitrogen relative to the total nitrogen, the percentage of amino nitrogen, the nitrate concentrations and the levels of phosphorus, phosphates and potassium.

In these figures, the columns A represent untreated litters, in place for 2 weeks, the columns B, C and D represent litters treated with a bacterial complex according to Example 4, in place for 7 weeks (columns B), in place for 16 weeks (columns C) and in place for 12 weeks and stored for 8 weeks (columns D).

Figure 22:
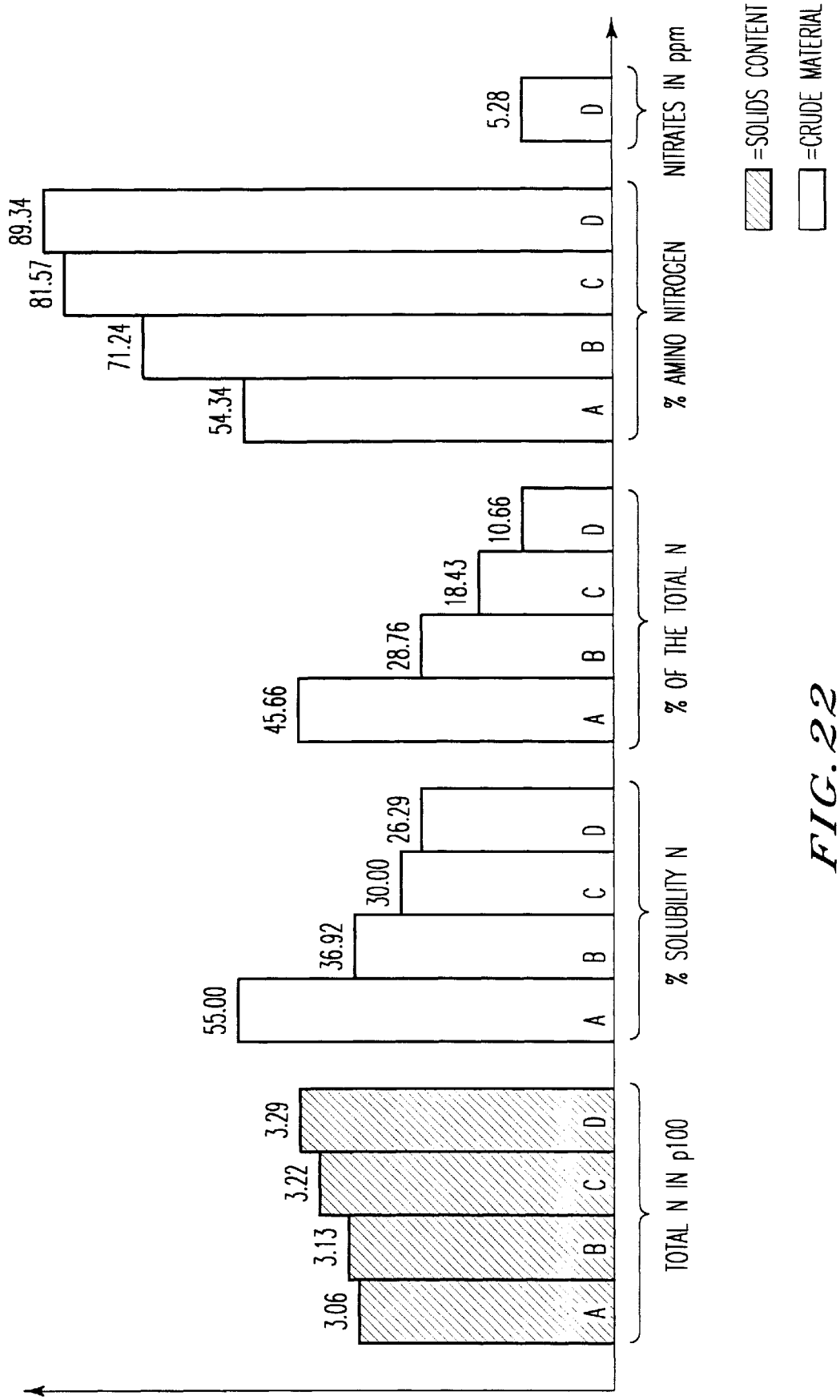
FIG. 22: results from Example 13.

These figures show that after treatment with a bacterial complex in accordance with the invention, there is stabilization of the nitrogen, a significant decrease in the nitrogen in soluble form and an increase in the percentage of amino nitrogen (FIG. 22).

Figure 24:
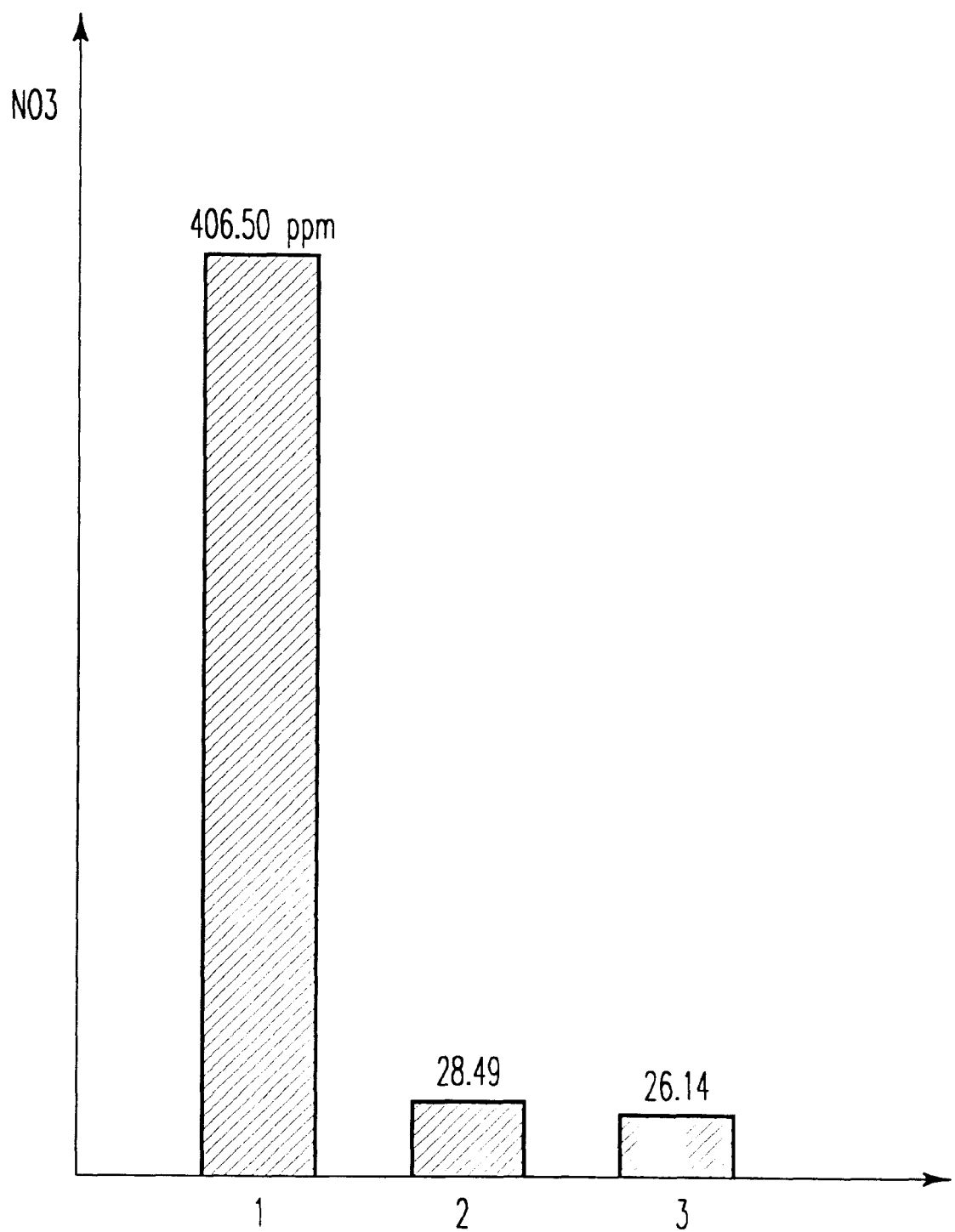
FIG. 24: the change in the nitrate content of manueres in Example 13.

Moreover, whereas normal putrefaction leads to hydrolysis and a decrease in the solids content, the treatment in accordance with the invention makes it possible to prevent such a decrease (FIG. 21).

c) Comparison of the nitrate contents of differently treated manures:

FIG. 24 illustrates more precisely the change in the nitrate content of manures, according to the treatment to which they have been subjected.

Column 1 corresponds to manure treated with a commercial product (BIO-SUPER®), column 2 corresponds to a litter in place treated with a bacterial complex according to Example 7, before composting, and column 3 illustrates the nitrate levels obtained on litters treated and composted in accordance with the invention.

This figure shows the capacity of the bacterial complexes in accordance with the invention to use nitrates as a source of nitrogen.

Figure 25:
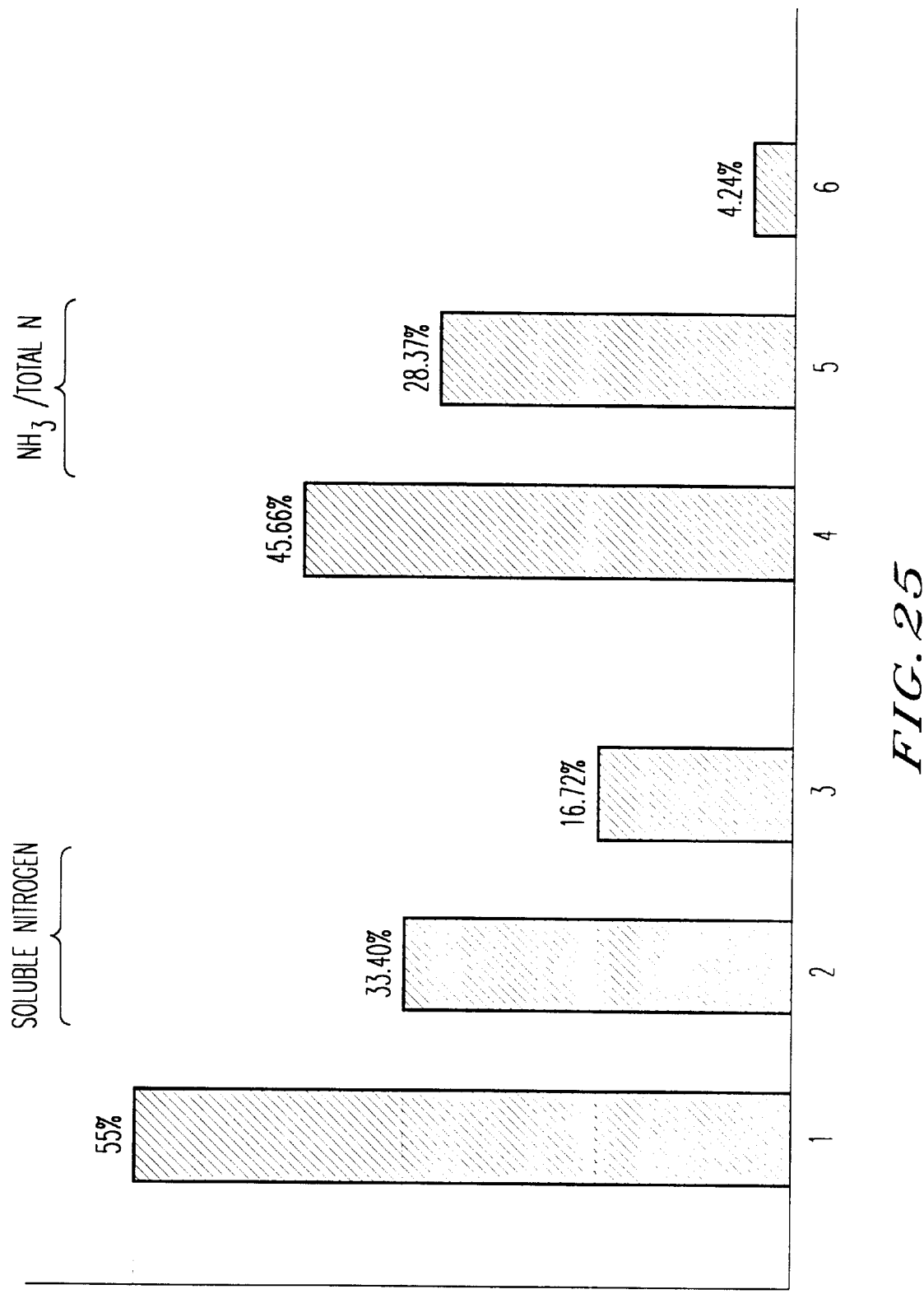
FIG. 25: the change in soluble nitrogen from Example 13.

FIG. 25 illustrates the advantage of the composting of manure in order to limit the pollution of water tables and shows, in particular, the significant decrease in soluble nitrogen and in aqueous ammonia in a manure treated and composted in accordance with the invention.

Figure 26:
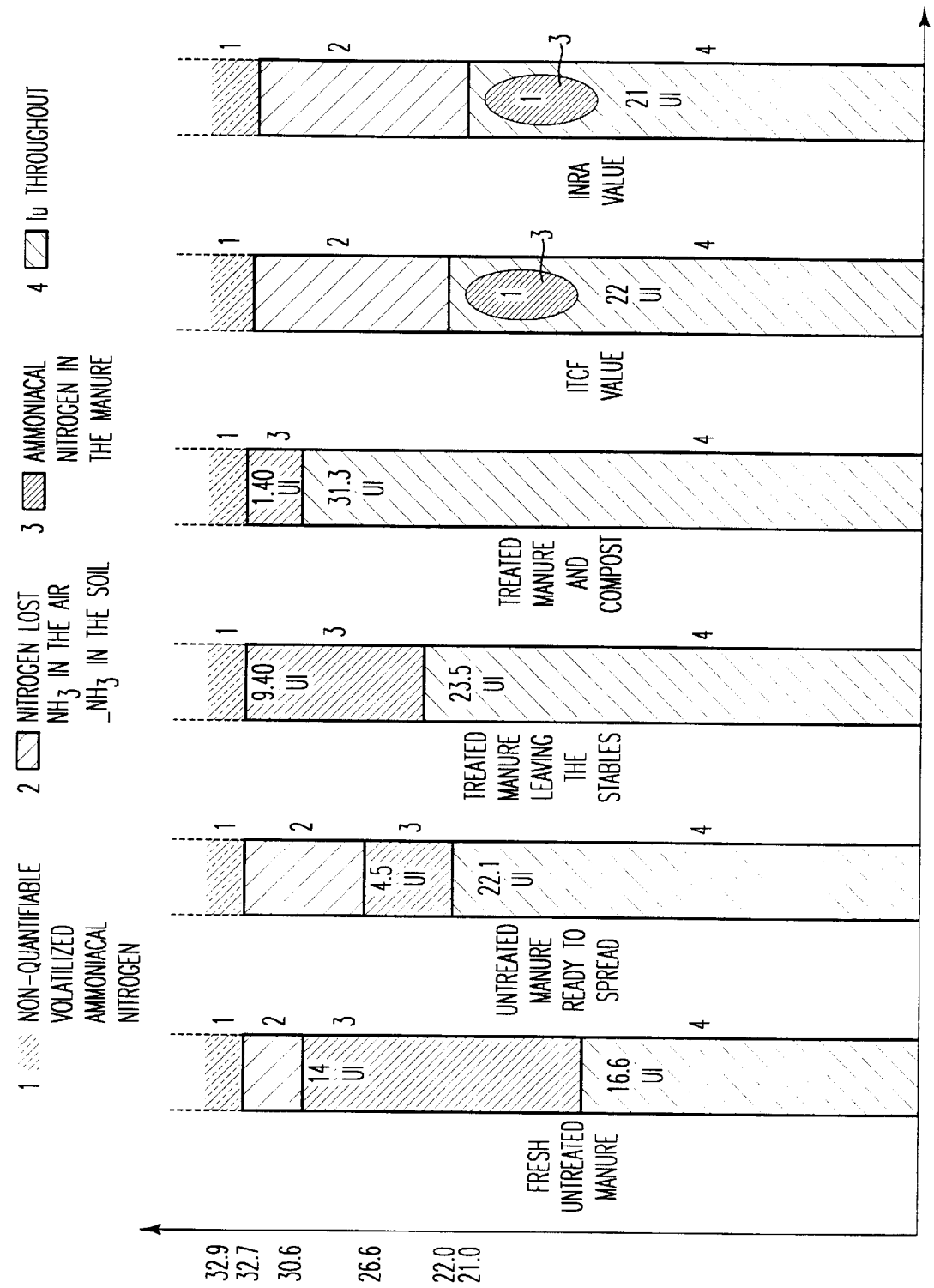
FIGS. 26–28: the comparative change in and distribution of nitrogen from Example 13.
Figure 27:
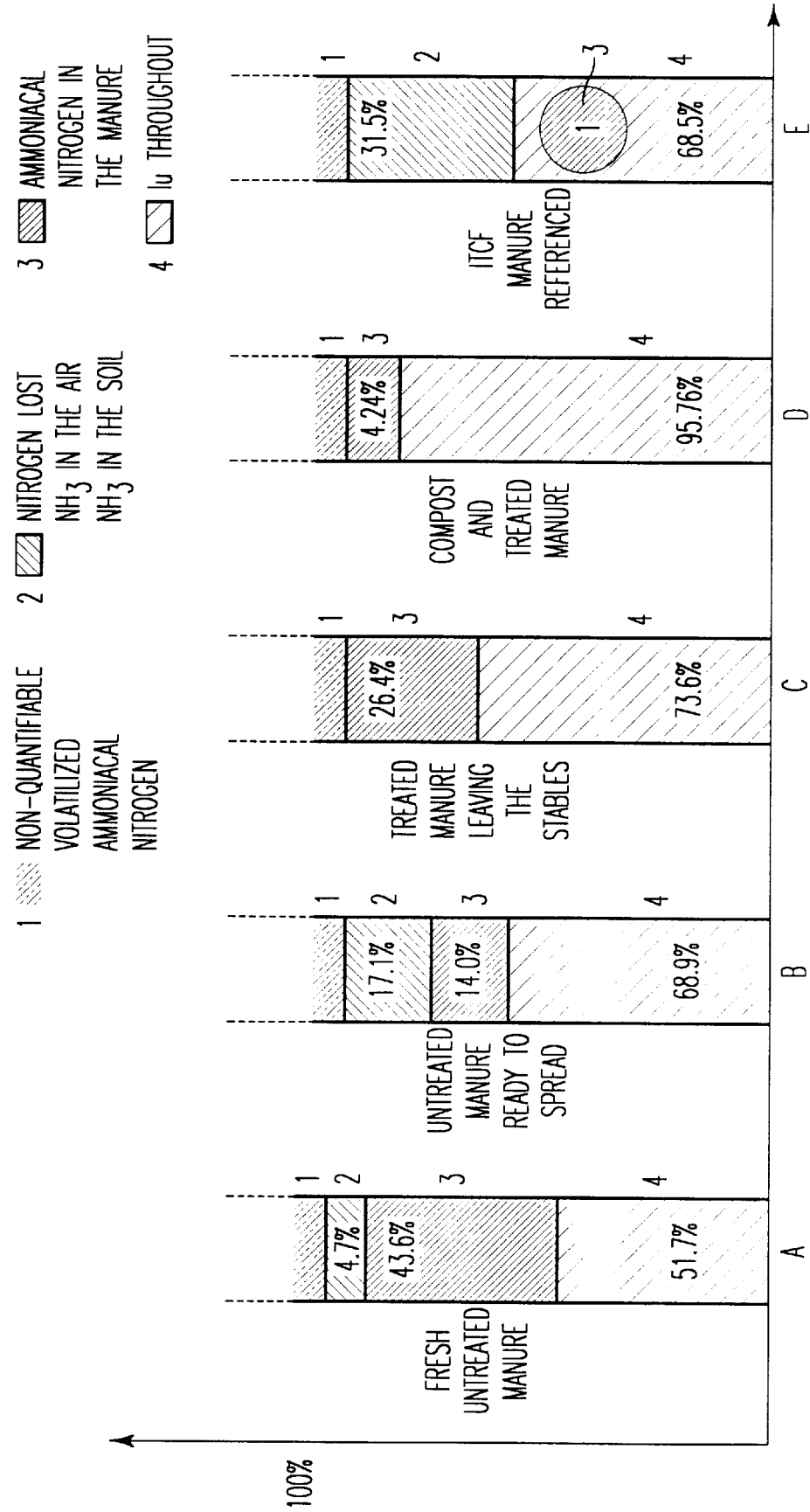
Figure 28:
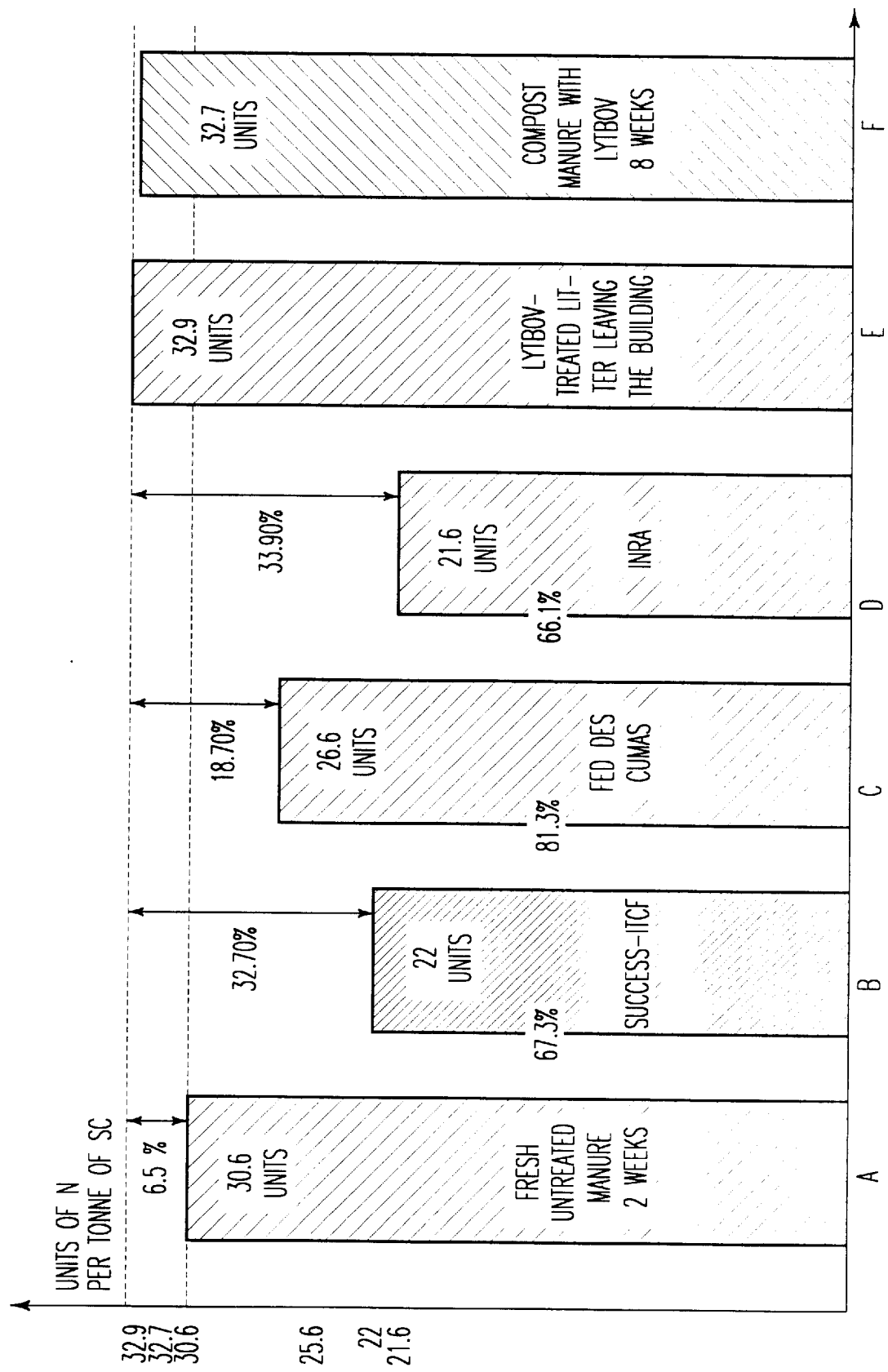

In this figure, columns 1 to 3 illustrate the change in soluble nitrogen: column 1 illustrates the amount of soluble nitrogen (as a percentage) of a control manure (55%), column 2 illustrates the amount of soluble nitrogen (as a percentage) of a control manure treated in place but not composted with a bacterial complex according to Example 7 (33.4%) and column 3 illustrates the amount of soluble nitrogen (as a percentage) of a litter treated and composted with a bacterial complex according to Example 7 (16.72%); columns 4 to 6 illustrate the change in the aqueous ammonia/total nitrogen ratio (as a percentage): column 4 illustrates this ratio for a control manure (45.66%) which corresponds to 83% of soluble nitrogen, column 5 illustrates the said ratio for a litter treated in place with a bacterial complex according to Example 7 but not composted (28.37%), which corresponds to 84.9 % of soluble nitrogen and column 6 illustrates the same ratio for a litter treated and composted with a bacterial complex according to Example 7 (4.24%), which corresponds to 25.4% of soluble nitrogen.

d) Values and distribution of the nitrogen in cattle manures: comparative study:

FIGS. 26, 27 and 28 show the comparative change in and distribution of nitrogen: standard values and values obtained with a manure treated in accordance with the invention.

In FIGS. 26 and 27, the nitrogen istribution is as follows:
(1) non-quantifiable volatilized ammoniacal nitrogen,
(2) lost nitrogen: NH$_3$ in the air, NH$_3$ in the soil,
(3) ammoniacal nitrogen in the manure,
(4) proteinic nitrogen.

In FIG. 26, the results are expressed as values, whereas in FIG. 27, they are expressed as a percentage.

In these two figures, column A corresponds to a fresh, untreated control manure, column B corresponds to an untreated, ready-to-spread control manure, column C corresponds to a manure treated in accordance with the invention, leaving the stables, column D corresponds to a manure treated and composted in accordance with the invention, columns E (FIGS. 26 and 27) and F (FIG. 26) are standard values supplied by the ITCF (column E) and the INRA (column F).

These FIGS. 26 and 27 show:
the absence of lost nitrogen in a manure treated in accordance with the invention (columns C and D),
a very low presence of ammoniacal nitrogen in a manure treated and composted according to the invention (column D) (4.24% compared with 31.5% for the ITCF manure (column E)) and a large amount of proteinic nitrogen (95.76%) (column D).

FIG. 28 gives the comparative values of nitrogen/solids content: control manure (column A), ITCF values (columns B and C), INRA values (column D) and values according to the invention (columns E and F) and illustrates the absence of loss of nitrogen in a manure treated in accordance with the invention.

As emerges from the preceding text, the invention is in no way limited to the modes of implementation, of production and of application thereof which have just been described in greater detail; on the contrary, it encompasses all the variants which may occur to those skilled in the art, without departing from the context or the scope of the present invention.

I claim:

1. A process for converting an organic nitrogenous compound of low molecular weight or an inorganic nitrogenous compound into protein, comprising the step of contacting the organic nitrogenous compound or the inorganic nitrogenous compound with a viable bacterial complex comprising at least one viable non-pathogenic Bacillus species selected from the group consisting of *Bacillus subtilis, Bacillus amyoliquefaciens, Bacillus megaterium, Bacillus licehniformis,* and *Bacillus circulans*, and at least one viable non-pathogenic Lactobacillus species selected from the group consisting of *Lactobacillus rhamnosus, Lactobacillus paracasei, Lactobacillus fermentum*, and *Lactobacillus acidophilus*, wherein the complex has the characteristic of having the capacity to convert the organic nitrogenous compound or the inorganic nitrogenous compound into protein, thereby converting the organic nitrogenous compound or the inorganic nitrogenous compound into protein.

2. The process of claim 1, wherein the organic nitrogenous compound or the inorganic nitrogenous compound is from animal waste.

3. The process of claim 2, wherein the animal is monogastric.

4. The process of claim 3, wherein the animal is a poultry animal.

5. The process of claim 1 wherein the organic nitrogenous compound or the inorganic nitrogenous compound is from poultry litters.

6. The process of claim 1, wherein the viable bacterial complex is biologically pure.

7. A viable bacterial complex comprising at least one viable non-pathogenic Bacillus species selected from the group consisting of *Bacillus subtilis, Bacillus amyoliquefaciens, Bacillus megaterium, Bacillus licheniformis,* and *Bacillus circulans*, and at least one viable non-pathogenic Lactobacillus species selected from the group consisting of *Lactobacillus rhamnosus, Lactobacillus paracasei, Lactobacillus fermentum*, and *Lactobacillus acidophilus*, wherein the complex has the characteristic of having the capacity to convert an organic nitrogenous compound of low molecular weight or an inorganic nitrogenous compound into protein, and wherein the ratio of the Lactobacillus species to the Bacillus species is between 1 to 100 and 100 to 1.

8. The bacterial complex of claim 7, wherein the organic nitrogenous compound is selected from the group consisting of urea, urates, amino acids, and nitrogenous bases.

9. The bacterial complex of claim 7, wherein the inorganic nitrogenous compound is selected from the group consisting of ammonia, nitrates, and nitrites.

10. The bacterial complex of claim 7, wherein the complex has at least one enzymatic activity selected from the group consisting of cellulolytic activity, proteolytic activity, amylolytic activity, lipolytic activity, and pectinolytic activity.

11. The bacterial complex of claim 7, wherein the ratio of the Lactobacillus species to the Bacillus species is between 1 to 10 and 10 to 1.

12. The bacterial complex of claim 7, wherein the ratio of the Lactobacillus species to the Bacillus species is between 1 to 10 and 1 to 1.

13. The bacterial complex of claim 7, wherein the ratio of the Lactobacillus species to the Bacillus species is about 1 to 1.

14. The bacterial complex of claim 7, comprising more than one Bacillus species and more than one Lactobacillus species, wherein the ratio of one of the Bacillus species to another of the Bacillus species is between 1 to 1 and 1 to 100, and the ratio of one of the Lactobacillus species to another of the Lactobacillus species is between 1 to 1 and 1 to 100.

15. The bacterial complex of claim 7, wherein the total concentration of the Bacillus species and the Lactobacillus species is between $1\times10^2$ cfu/g and $1\times10^8$ cfu/g.

16. The bacterial complex of claim 7, wherein the concentration of the Bacillus species is between $1\times10^2$ cfu/g and $1\times10^7$ cfu/g and the concentration of the Lactobacillus species is between $1\times10^2$ cfu/g and $1\times10^8$ cfu/g.

17. The bacterial complex of claim 16, wherein the concentration of the Lactobacillus species is between $1\times10^3$ cfu/g and $1\times10^8$ cfu/g.

18. The bacterial complex of claim 17, comprising *Bacillus subtilis* and *Bacillus megaterium*.

19. The bacterial complex of claim 16, wherein the Bacillus is *Bacillus subtilis*.

20. The bacterial complex of claim 19, wherein the concentration of the Bacillus species is at least $1\times10^3$ cfu/g.

21. The bacterial complex of claim 20, wherein urates are the organic nitrogenous compound.

22. The bacterial complex of claim 7, comprising *Bacillus subtilis, Bacillus amyloliquefaciens, Bacillus megaterium, Bacillus licheniformis, Bacillus circulans, Lactobacillus rhammosus, Lactobacillus paracasei, Lactobacillus fermentum*, and *Lactobacillus acidophilus*.

23. The bacterial complex of claim 7, further comprising a non-pathogenic Pediococcus.

24. The bacterial complex of claim 7, further comprising at least one neutral diluent.

25. The bacterial complex of claim 7, further comprising a chemical tracer or a microbiological tracer.

26. The viable bacterial complex of claim 7, which is biologically pure.

* * * * *